(12) United States Patent
Tal et al.

(10) Patent No.: US 10,398,875 B2
(45) Date of Patent: Sep. 3, 2019

(54) EMBOLIZATION MICROCATHETER

(71) Applicant: ACCURATE MEDICAL THERAPEUTICS LTD., Tel-Aviv (IL)

(72) Inventors: Michael Gabriel Tal, Savyon (IL); Eran Miller, Moshav Beit Elazari (IL)

(73) Assignee: Accurate Medical Therapeutics Ltd., Tel-Aviv (IL)

( * ) Notice: Subject to any disclaimer, the term of this patent is extended or adjusted under 35 U.S.C. 154(b) by 0 days.

(21) Appl. No.: 15/542,427

(22) PCT Filed: Jan. 8, 2016

(86) PCT No.: PCT/IB2016/050087
§ 371 (c)(1),
(2) Date: Jul. 9, 2017

(87) PCT Pub. No.: WO2016/110824
PCT Pub. Date: Jul. 14, 2016

(65) Prior Publication Data
US 2017/0368306 A1    Dec. 28, 2017

Related U.S. Application Data

(60) Provisional application No. 62/127,036, filed on Mar. 2, 2015, provisional application No. 62/101,637, filed on Jan. 9, 2015.

(51) Int. Cl.
*A61M 5/00* (2006.01)
*A61M 25/00* (2006.01)
(Continued)

(52) U.S. Cl.
CPC ... *A61M 25/0068* (2013.01); *A61B 17/12109* (2013.01); *A61B 17/12186* (2013.01);
(Continued)

(58) Field of Classification Search
CPC ............ A61M 25/0068; A61M 25/007; A61M 25/0021; A61M 25/0027;
(Continued)

(56) References Cited

U.S. PATENT DOCUMENTS 5,749,894 A * 5/1998 Engelson .......... A61B 17/12022
128/898
5,833,671 A   11/1998 Macoviak et al.
(Continued)

FOREIGN PATENT DOCUMENTS

AT    1857134 A1 * 11/2007 ........ A61M 25/0013
EP    2777738         9/2014
(Continued)

OTHER PUBLICATIONS

International Search Report of PCT/IB2016/050087 Completed Mar. 15, 2016; dated Mar. 22, 2016 4 pages.
(Continued)

*Primary Examiner* — Edelmira Bosques
(74) *Attorney, Agent, or Firm* — The Roy Gross Law Firm, LLC; Roy Gross

(57) ABSTRACT

Microcatheter for delivering a substance (e.g., infusion agent including embolization material and/or contrast enhancing material) in a small blood vessel towards a target bodily part. Includes a single lumen surrounded by tubular wall having outer diameter and opened at both ends; tubular wall proximal portion is connectable to a pressure source and reservoir containing infusion agent, and tubular wall distal portion ends with a tip; the tubular wall distal portion includes an infusion agent flow disruption section configured to disrupt passage therethrough of incoming retrograded flow of infusion agent, during continuous delivery of infusion suspension from the reservoir to the tip. Disclosed are methods using the microcatheter for performing local
(Continued)

embolization in a small blood vessel feeding a (for example, cancerous) target bodily part, and for delivering infusion agent in a small blood vessel towards such target bodily part. Also disclosed are devices and methods for filtering non-target infusion agent.

20 Claims, 9 Drawing Sheets

(51) Int. Cl.
    *A61M 31/00*     (2006.01)
    *A61B 17/12*     (2006.01)
    *A61B 17/00*     (2006.01)

(52) U.S. Cl.
    CPC ........ *A61M 5/007* (2013.01); *A61M 25/0021* (2013.01); *A61M 25/0067* (2013.01); *A61M 25/0074* (2013.01); *A61M 25/0075* (2013.01); *A61B 2017/00345* (2013.01); *A61B 2017/00884* (2013.01); *A61B 2017/00893* (2013.01); *A61B 2017/1205* (2013.01); *A61M 25/007* (2013.01); *A61M 25/0054* (2013.01); *A61M 31/005* (2013.01); *A61M 2025/0024* (2013.01); *A61M 2025/0042* (2013.01); *A61M 2025/0057* (2013.01); *A61M 2025/0073* (2013.01); *A61M 2025/0079* (2013.01); *A61M 2025/0096* (2013.01); *A61M 2205/7545* (2013.01)

(58) Field of Classification Search
    CPC ....... A61M 25/0074–0075; A61M 2025/0188; A61M 2025/0183; A61B 17/12109; A61B 17/12186
    See application file for complete search history.

(56) References Cited

U.S. PATENT DOCUMENTS

| | | |
|---|---|---|
| 5,964,223 A | 10/1999 | Baran |
| 8,500,775 B2 | 8/2013 | Chomas et al. |
| 2002/0197246 A1* | 12/2002 | Toombs .............. A61K 38/4886 424/94.63 |
| 2004/0122362 A1 | 6/2004 | Houser et al. |
| 2007/0225634 A1 | 9/2007 | Ferren et al. |
| 2008/0039786 A1 | 2/2008 | Epstein et al. |
| 2008/0188831 A1 | 8/2008 | Bonnette et al. |
| 2008/0188928 A1 | 8/2008 | Salahieh et al. |
| 2011/0245766 A1 | 10/2011 | Leonard et al. |
| 2011/0251629 A1* | 10/2011 | Galdonik .............. A61B 17/221 606/159 |
| 2012/0041419 A1 | 2/2012 | Blanchard et al. |

FOREIGN PATENT DOCUMENTS

| | | |
|---|---|---|
| WO | 97/21455 | 6/1997 |
| WO | 01/32240 | 5/2001 |
| WO | 2008067362 | 6/2008 |
| WO | 2009132065 | 10/2009 |
| WO | 2010/026578 | 3/2010 |
| WO | 2010/125159 | 11/2010 |
| WO | 2011091275 | 7/2011 |
| WO | 2013184782 | 12/2013 |
| WO | 2014047179 | 3/2014 |
| WO | 2015195625 | 12/2015 |

OTHER PUBLICATIONS

Written Opinion of International Searching Authority of PCT/IB2016/050087 Completed Mar. 15, 2016; dated Mar. 22, 2016 6 pages.

* cited by examiner

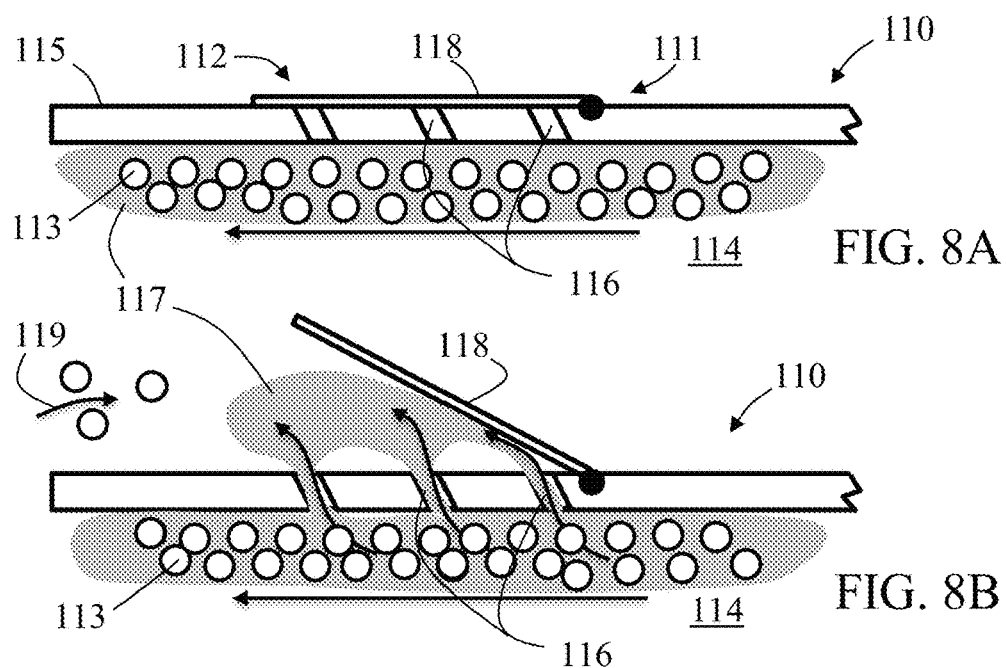
FIG. 8A
FIG. 8B
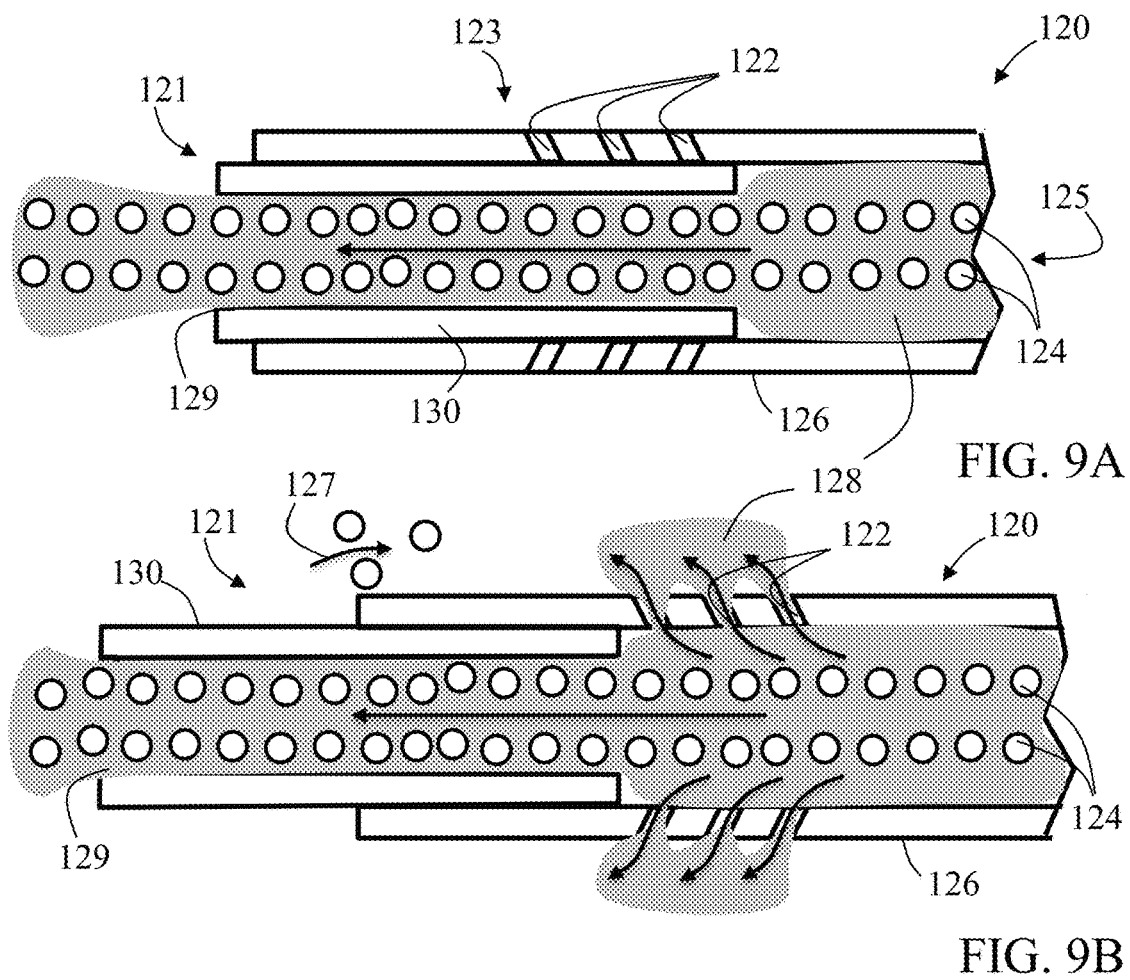
FIG. 9A
FIG. 9B

EMBOLIZATION MICROCATHETER

FIELD OF THE INVENTION

The present invention, in some embodiments thereof, relates to microcatheters and methods for delivering a substance (e.g., an infusion agent including embolization material and/or contrast enhancing material) to a target bodily part, for example, located within the cardiovascular system, and in particular to an embolization microcatheter, uses thereof in performing local embolization procedures, and delivering an infusion agent (for example, embolization beads with contrast enhancing material). Some embodiments of the invention are applicable for: (i) delivering an infusion agent including embolization material and/or contrast enhancing material in a small blood vessel towards a target bodily part, and (ii) performing local embolization in a small blood vessel feeding a (for example, cancerous) target bodily part, thereby forming emboli in small blood vessels, while preventing or minimizing non-target embolization (associated with contrast enhancing material). Some embodiments of the invention also relate to devices and methods for filtering non-target infusion agent (e.g., embolization material and/or contrast enhancing material).

BACKGROUND OF THE INVENTION

The purpose of embolization is to prevent blood flow to an area of the body, which can effectively shrink a tumor or block an aneurysm, commonly carried out as an endovascular procedure. Access to the organ in question is acquired by means of a guidewire and catheter(s). The position of the correct artery or vein supplying the pathology in question can be located by digital subtraction angiography (DSA), producing images are then used as an accessing map to the correct vessel. The artificial embolus can be made by using coils, particles, foam, plug, microspheres or beads. Once the artificial emboli have been successfully introduced, another set of DSA images are taken to confirm a successful deployment.

Transarterial embolization therapy, tumor embolization, or transcatheter arterial embolization (TAE), involve administration of embolization material (which may include chemotherapeutics or/and radiotherapeutics) directly to a tumor typically associated with a target bodily part, such as an organ (for example, the liver), via a catheter. These techniques are usually performed using a microcatheter which targets the tumor, while attempting to avoid dispersion of embolization material to healthy organs.

Embolization of tumors is usually performed using microcatheters for different reasons. At first, there is a requirement for localized embolization for effecting primarily the tumor and as little healthy tissue as possible. One of the problems associated with embolization is commonly known as "non-target embolization", where the embolic material travels to small blood vessels other than to those which directly feed the target tumor or region. This can damage healthy tissues in these areas, often resulting in serious complications. Possible scenarios include gastric ulcers with liver embolization, as well as cases where embolic material refluxes alongside the microcatheter reaching the wall of the stomach, possibly causing ischemia and ulceration. An additional phenomenon, which is abundant, especially, in advanced stage liver cancer, is non-target embolization through arterioportal shunt.

A microcatheter is usually passed via a larger-lumen catheter, which is placed within the proximal part of the vessel, such as the celiac or hepatic artery, and the microcatheter is then advanced therethrough towards the tumor until reaching an effective distance for the embolization. It is advantageous to use a diagnostic catheter as the delivery medium for the microcatheter, by not replacing it with a larger diameter sheath, for example, therefore saving substantial time. The inner lumen of the diagnostic catheter is very small, usually 0.035 and up to 0.038 inches, so that the microcatheter should be about 1 mm or less in outer diameter.

Another reason that microcatheters are routinely used in embolization procedures is the size of the feeding vessels, which carry blood directly to the organ and tumor. In order to get as close as possible to the tumor, the embolization catheter is advanced into smaller and sometime tortuous vessels. These vessels cannot be accessed with a larger and often stiffer catheter. Also, blood vessels in the body tend to go into spasm when manipulated, causing an ineffective embolic material delivery, so flexible micro-sized catheters are preferred to avoid such scenarios.

SUMMARY OF THE INVENTION

The present invention, in some embodiments thereof, relates to microcatheters and methods for delivering a substance (e.g., an infusion agent including embolization material and/or contrast enhancing material) to a target bodily part, for example, located within the cardiovascular system, and in particular to an embolization microcatheter, uses thereof in performing local embolization procedures, and delivering an infusion agent (for example, embolization beads with contrast enhancing material). Some embodiments of the invention are applicable for: (i) delivering an infusion agent including embolization material and/or contrast enhancing material in a small blood vessel towards a target bodily part, and (ii) performing local embolization in a small blood vessel feeding a (for example, cancerous) target bodily part, thereby forming emboli in small blood vessels, while preventing or minimizing non-target embolization (associated with contrast enhancing material). Some embodiments of the invention also relate to devices and methods for filtering non-target infusion agent (e.g., embolization material and/or contrast enhancing material).

According to an aspect of some embodiments of the present invention, there is provided an embolization microcatheter for delivering an infusion agent in a small blood vessel towards a target bodily part, the microcatheter comprising: a single lumen surrounded by a tubular wall having an outer diameter and opened at both ends; a proximal portion of the tubular wall is connectable to a pressure source and to a reservoir configured for containing an infusion suspension of the infusion agent in an infusion fluid, and a distal portion of the tubular wall ends with a tip; the tubular wall distal portion comprises an infusion agent flow disruption section applicable via the lumen and configured, when applied, to disrupt passage of an incoming retrograded flow of the infusion agent around periphery of the tubular wall distal portion adjacent thereto, during a continuous delivery of the infusion suspension from the reservoir to the tip. The use of a microcatheter having a single lumen only, for delivering the infusion suspension together with disrupting retrograded flow, optionally selectively or in reaction to change is surroundings (e.g., elevation of ambient pressure above a certain degree), is advantageous, for example, for keeping the microcatheter structure as small as possible, therefore having it fit for passage through a larger-sized catheter or/and into small blood vessels.

According to some embodiments of the invention, the flow disruption section is configured to diminish velocity of the incoming retrograded flow of the infusion agent, to divert or block the incoming retrograded flow of the infusion agent, to cause turbulence or vortex in the incoming retrograded flow of the infusion agent, or/and to increase local pressure thereabout.

According to some embodiments of the invention, the flow disruption section is configured for the disruption by injecting a portion of the infusion fluid against the retrograded flow, the flow disruption section comprises a plurality of openings distributed around or/and along the flow disruption section, each opening is shaped or/and sized to allow passage therethrough of the infusion fluid of the infusion suspension, and to block passage therethrough of the infusion agent of the infusion suspension.

According to some embodiments of the invention, at least one of the openings comprises a slit with a gap having a maximal cross sectional dimension less than minimal diameter of the infusion agent. According to some embodiments of the invention, at least one of the openings comprises a pore having a maximal cross sectional dimension less than minimal diameter of the infusion agent.

According to some embodiments of the invention, the maximal cross sectional dimension is equal to or less than about 100 microns, or optionally is equal to or less than about 30 microns. According to some embodiments of the invention, the pore is located at end of a channel being angled relative to a long axis of the lumen or/and relative to a radial axis thereof at a cross section adjacent thereto.

According to some embodiments of the invention, the microcatheter includes at least two of the pores angularly located in different directions such that a first stream of the infusion fluid in immediate vicinity of a first one of the pores at least partially intersects a second stream of the infusion fluid in immediate vicinity of a second one of the pores.

According to some embodiments of the invention, the flow disruption section comprises material being firmer than material of other sections of the tubular wall distal portion. According to some embodiments of the invention, the flow disruption section is made of a metallic material, a hard polymeric material, or a combination thereof.

According to some embodiments of the invention, the flow disruption section comprises a plurality of projections branching out from and distributed around or/and along the flow disruption section. According to some embodiments of the invention, the projections are flexible. According to some embodiments of the invention, the projections are configured to bend proximally into a straight form along the tubular wall distal portion when the flow disruption section is passed distally within a closely fitting outer tube. According to some embodiments of the invention, the projections are curled distally towards the tip when in a relaxed configuration. According to some embodiments of the invention, the projections are in a form of threads, prongs, or bulges.

According to some embodiments of the invention, the flow disruption section comprises material being thinner than material of other sections of the tubular wall distal portion. According to some embodiments of the invention, the flow disruption section comprises material being more flexible than material of other sections of the tubular wall distal portion. According to some embodiments of the invention, the microcatheter is configured as a single integrated structure, wherein the tubular wall includes, and is structurally continuous with, the flow disruption section as a single member.

According to some embodiments of the invention, the tubular wall outer diameter is equal to or less than about 1 mm. According to some embodiments of the invention, the tubular wall is configured for insertion into the small blood vessel originating from a celiac or hepatic artery. According to some embodiments of the invention, the tubular wall is configured for the delivery of the infusion agent to the target bodily part being a tumor or cancerous tissue.

According to some embodiments of the invention, the flow disruption section is shaped to induce turbulent flow in distal approximation thereto upon flow of the infusion agent away from the target bodily part and towards the tip of the tubular wall distal portion. According to some embodiments of the invention, the tubular wall distal portion tip includes the flow disruption section.

According to some embodiments of the invention, the flow disruption section is pressure sensitive and configured to disrupt the incoming retrograded flow of the infusion agent only when pressure inside the tubular wall distal portion equals a predetermined pressure.

According to some embodiments of the invention, the microcatheter further comprises a valve mechanism configured to cover side openings provided at the flow disruption section when pressure inside the tubular wall distal portion is less than the predetermined pressure, and to uncover the side openings when pressure inside the tubular wall distal portion is greater than the predetermined pressure.

According to some embodiments of the invention, the flow disruption section is configured to stretch from a first average diameter to a second average diameter greater than the tubular wall outer diameter when pressure inside the tubular wall distal portion equals the predetermined pressure, and to collapse back to the first average diameter when the pressure inside the tubular wall distal portion is less than the predetermined pressure, during the continuous delivery of the infusion suspension from the reservoir to the tip before, during, and after the stretching and collapsing.

According to some embodiments of the invention, the tubular wall is sized for unhindered insertion into the small blood vessel having a first average ambient pressure upon the tubular wall placement therein, and configured for the delivery of the infusion suspension thru the lumen and the tip when the pressure inside the tubular wall distal portion is a first inner pressure being less than the predetermined expansion pressure and greater than the first average ambient pressure, wherein the flow disruption section is configured such that upon elevation to a second average ambient pressure within the small blood vessel, being equal to or greater than the first inner pressure, and upon accumulation of the infusion suspension between the tip and the target bodily part, the pressure inside the tubular wall distal portion increases to a second inner pressure being equal to or greater than the predetermined expansion pressure, whereby the flow disruption section stretches to the second average diameter.

According to some embodiments of the invention, the microcatheter is configured such that, under a selected third inner pressure being greater than the first inner pressure and less than the second inner pressure, the flow disruption section stretches in response to a systole and collapses in response to a diastole, relative to the second average ambient pressure. According to some embodiments of the invention, the predetermined pressure is greater than 50 mm Hg.

According to some embodiments of the invention, the flow disruption section is configured to expand from the first average diameter to a maximal average diameter greater than inner diameter of the small blood vessel in direct blood communication with the target bodily part. According to some embodiments of the invention, the flow disruption section is configured to expand to a maximal average diameter being less than inner diameter of the small blood vessel in direct blood communication with the target bodily part.

According to some embodiments of the invention, the flow disruption section comprises material being permeable to the infusion fluid and impermeable to the infusion agent, such that when the flow disruption section stretches to the second average diameter, the impermeable material allows flowing of the infusion fluid therethrough and prevents passage and flowing of the infusion agent therethrough.

According to some embodiments of the invention, the flow disruption section includes a sub-section having at least one opening sized to allow passage therethrough of the infusion agent when the flow disruption section is at least partially stretched. According to some embodiments of the invention, the at least one opening is configured to obstruct and prevent flow therethrough of the infusion agent when the flow disruption section is at the first average diameter. According to some embodiments of the invention, the at least one opening is directed at least partially in a distal direction of the tubular wall or/and towards the tip.

According to an aspect of some embodiments of the present invention, there is provided a method for performing local embolization in a small blood vessel feeding a cancerous target bodily part, the method comprising: providing an embolization microcatheter comprising a tubular wall having an outer diameter, enclosing a single lumen extending therealong, and including a distal portion ending with a tip opened to the lumen with a distal outlet, the tubular wall distal portion comprises an infusion agent flow disruption section applicable via the lumen and configured to disrupt passage around periphery of the distal portion of an incoming retrograded flow of infusion agent, during a continuous delivery of an infusion suspension of the infusion agent in an infusion fluid through the lumen to the tip; locating the target bodily part and the small blood vessel using an imaging technique; providing a catheter in close proximity to a proximal entry to the small blood vessel or to an interim blood vessel opened to the small blood vessel downstream thereto, the catheter comprises a hollow passage opened to the small blood vessel and has an inner diameter equal to or less than about 1 mm; passing the microcatheter through the hollow passage and into the small blood vessel, whereby the small blood vessel reaches a first average ambient pressure upon the tubular wall placement therein; delivering the infusion suspension through the lumen and the distal outlet to the target bodily part; accumulating the infusion suspension between the microcatheter tip and the target bodily part, characterized by an increase of pressure within the small blood vessel to a second average ambient pressure; and allowing or/and applying the infusion agent flow disruption section to disrupt an incoming retrograded flow of the infusion agent passing therethrough during the continuous delivery of the infusion suspension through the lumen to the tip, by diminishing, blocking or/and causing turbulence in the incoming retrograded flow of the infusion agent.

According to some embodiments of the invention, in the method, the flow disruption section comprises a plurality of openings distributed around or/and along the flow disruption section, each opening is shaped or/and sized to allow passage therethrough of the infusion fluid of the infusion suspension, and to block passage therethrough of the infusion agent, in a form of beads, of the suspension, wherein the delivering comprises infusing a volume of the infusion fluid through the side openings while blocking the beads from passing through the side openings, whereby during the allowing, the infused volume of the infusion fluid effects the disrupting of the incoming retrograded flow of the infusion agent.

According to some embodiments of the invention, in the method, the infusion agent flow disruption section is pressure sensitive, wherein the method further includes: pressurizing the lumen so as to allow the pressure inside the tubular wall distal portion to become equal to or exceed a predetermined pressure, whereby the flow disruption section stretches outwardly and effects the disruption of the passage therethrough of the incoming retrograded flow of the infusion agent, during the continuous delivery of the infusion suspension through the lumen to the tip.

According to some embodiments of the invention, in the method, the pressurizing actuates the flow disruption section to diminish, block, or/and cause turbulence in, the incoming retrograded flow of the infusion agent, thereby increasing local pressure thereabout. According to some embodiments of the invention, in the method, the pressurizing is performed until the infusion agent occludes the small blood vessel or/and until a selected pressure difference is developed between the tubular wall distal portion and the target bodily part.

According to some embodiments of the invention, the method comprises repeating at least one of the accumulating and the pressurizing until forming a chosen sized embolus between the tip and the target bodily part.

According to some embodiments of the invention, in the method, the locating includes delivering contrast enhancing material to the small blood vessel through the hollow passage of the catheter.

According to an aspect of some embodiments of the present invention, there is provided a method for performing local embolization in a small blood vessel feeding a cancerous target bodily part, the method comprising: providing an embolization microcatheter comprising a tubular wall having an outer diameter, enclosing a single lumen extending therealong, and comprising a distal portion ending with a tip opened to the lumen with a distal outlet, the tubular wall distal portion comprises an infusion agent flow disruption section applicable via the lumen and configured to disrupt passage therethrough of an incoming retrograded flow of an infusion agent, during continuous delivery of an infusion suspension of the infusion agent in an infusion fluid through the lumen to the tip; passing the microcatheter into the small blood vessel until the tip of the microcatheter is located at a chosen distance from the target bodily part; delivering the infusion suspension via the distal outlet towards the target bodily part; allowing or/and applying the infusion agent flow disruption section to disrupt an incoming retrograded flow of the infusion agent passing therethrough during the continuous delivery of the infusion suspension through the lumen to the tip, by diminishing, blocking or/and causing turbulence in the incoming retrograded flow of the infusion agent; selecting a blood vessel portion upstream to the small blood vessel, and monitoring the blood vessel portion using an imaging technique; via the monitoring, detecting an indication of presence of the infusion fluid in the blood vessel portion; and in response to the detected indication, stopping the delivery of the infusion suspension.

According to some embodiments of the invention, in the method, the selecting of the blood vessel portion includes determining a required distance from the small blood vessel with a minimal effectively imaged quantity of the infusion fluid volume originating from the side openings and flowing into the blood vessel portion, before the infusion suspension originating from the distal outlet and reaching the blood vessel portion following blood flow reflux from the small blood vessel towards the blood vessel portion.

According to some embodiments of the invention, in the method, the required distance is at least about 10 mm. According to some embodiments of the invention, in the method, the infusion fluid includes a contrast enhancing agent. According to some embodiments of the invention, in the method, the infusing occurs following blood flow reflux from the small blood vessel towards the blood vessel portion. According to some embodiments of the invention, in the method, the infusing occurs during the delivery of the infusion suspension.

Unless otherwise defined, all technical or/and scientific terms used herein have the same meaning as commonly understood by one of ordinary skill in the art to which the invention pertains. Although methods and materials similar or equivalent to those described herein can be used in the practice or testing of embodiments of the invention, exemplary methods or/and materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 8A-8B are schematic partial side cut views of exemplary embodiments of a portion of an infusion agent flow disruption section that includes a covering mechanism, before (FIG. 8A) and after (FIG. 8B) actuation thereof, in accordance with some embodiments of the invention;

FIGS. 9A-9B are schematic side cut views of exemplary embodiments of the distal end of an exemplary microcatheter, particularly highlighting an exemplary embodiment of a valve mechanism configured to cover (FIG. 9A) and uncover (FIG. 9B) side openings included in an infusion agent flow disruption section, in accordance with some embodiments of the invention.

DESCRIPTION OF SPECIFIC EMBODIMENTS OF THE INVENTION

Figure 1A:
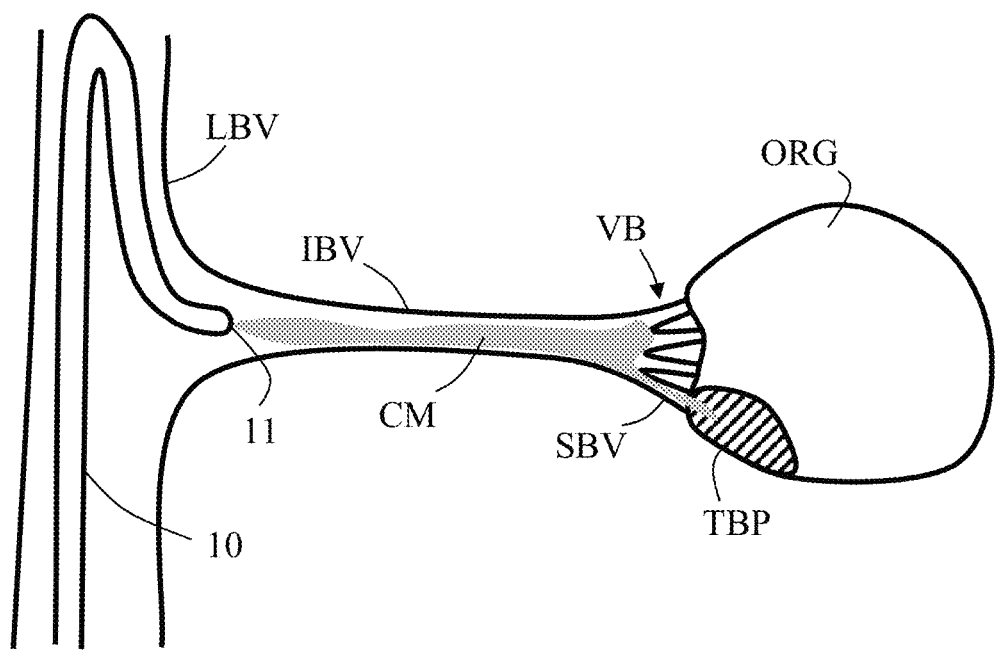
FIGS. 1A-1G are schematic side cut views representing possible scenarios of implementing exemplary embodiments of a method for performing local embolization in a small blood vessel feeding a target bodily part, in accordance with some embodiments of the invention.

The present invention, in some embodiments thereof, relates to microcatheters and methods for delivering a substance (e.g., an infusion agent including embolization material and/or contrast enhancing material) to a target bodily part, for example, located within the cardiovascular system, and in particular to an embolization microcatheter, uses thereof in performing local embolization procedures, and delivering an infusion agent (for example, embolization beads with contrast enhancing material). Some embodiments of the invention are applicable for: (i) delivering an infusion agent including embolization material and/or contrast enhancing material in a small blood vessel towards a target bodily part, and (ii) performing local embolization in a small blood vessel feeding a (for example, cancerous) target bodily part, thereby forming emboli in small blood vessels, while preventing or minimizing non-target embolization (associated with contrast enhancing material). Some embodiments of the invention also relate to devices and methods for filtering non-target infusion agent (e.g., embolization material and/or contrast enhancing material).

It is understood that the invention is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the invention. The following exemplary embodiments may be described in the context of exemplary embolization procedures for ease of description and understanding. However, the invention is not limited to the specifically described devices and methods, and may be adapted to various clinical applications without departing from the overall scope of the invention.

A limitation of using current micro-sized catheters for delivering an infusion agent (e.g., including embolization material, typically, with contrast enhancing material) is their inability to "push" the embolization material deeper into the tumor without applying excessive pressures. Over injection or forceful injection often cause back flow or/and dispersion of the infusion agent, potentially causing non-target embolization (associated with contrast enhancing material). Such backward flow or/and dispersion of embolization material during forceful injection can also be affiliated with inadvertent repositioning of the catheter.

In view of the preceding, and other, limitations associated with current embolization techniques, there is need for developing and practicing improved or/and new techniques (devices and methods) for delivering an infusion agent (e.g., including embolization material and/or contrast enhancing material) into small blood vessels located in close proximity to a target body part, while preventing or diminishing infusion agent (embolization material or/and contrast enhancing material) back flow or reflux from the small blood vessels.

The term "infusion agent", as used herein, refers to a substance that is suspended in a suspension fluid for forming an infusion suspension. The infusion suspension is supplied to, or provided in, a reservoir of a catheter and is infused (such as by injection) into a blood vessel of a subject.

In exemplary embodiments, the infusion agent is composed of, or includes, embolization (embolic) material or/and contrast media (such as contrast enhancing material or agent). In exemplary embodiments, the infusion agent is composed of, or includes, embolization (embolic) material, wherein the embolization material, in addition to having embolization properties, also has radio-opacity or/and radiographic properties. In exemplary embodiments, the infusion agent is composed of, or includes, contrast enhancing material, wherein the contrast enhancing material, in addition to having radio-opacity or/and radiographic properties, also has embolization properties. In exemplary embodiments, the infusion agent may be composed of, or include, any type or kind, and amount, of other material, having any type or kind of properties, suitable for infusing into a blood vessel of a subject.

In exemplary embodiments, the infusion suspension (including the infusion agent suspended in the infusion fluid) may be composed and formulated for being suitable in embolic type therapies, for example, intra-arterial embolic therapies. In some such embodiments, the infusion suspension may include the suspended infusion agent in the form of embolic beads for bland embolization. Optionally, alternatively or additionally, the infusion suspension may include the suspended infusion agent in the form of lipidol mixed with chemotherapeutic agents and embolic beads or/and chemotherapy drug eluting beads (e.g., polyvinyl alcohol microspheres loaded with doxorubicin, superabsorbent polymer microspheres—loaded with doxorubicin, or gelatin microspheres—loaded with cisplatin) for chemo-embolization. Optionally, alternatively or additionally, the infusion suspension may include the suspended infusion agent in the form of radioactive beads for radio-embolization.

In exemplary embodiments, embolization material may include at least one of liquid embolic agents (e.g., Onyx™ by Covidien, n-butyle-2-cyanoacrylate, or ethiodized oil), sclerosing agents (e.g., ethanol, ethanolamine oleate, or sodium tetradecyl sulfate), or particulate embolic agents (e.g., hemostatic absorbable gelatin, polyvinyl alcohol (PVA), acrylic gelatin microspheres, or glass). Embolization material may include radiopaque beads or/and drug eluting beads.

In exemplary embodiments, the suspension fluid includes a contrast enhancing material (agent), for example, diluted to a certain degree such as with saline. In some instances, the medical practitioner may mix together a viscous contrast enhancing material (agent) with embolization materials comprising saline and embolization beads (particles) or/and chemotherapeutic beads (particles), for example in a volumetric ratio of 50:50, thereby producing a fluidic suspension of beads and contrast enhancing material (agent) diluted to a chosen degree. In an exemplary embodiment, the suspension includes drug-eluting beads (DEB), chemotherapeutic material (e.g., doxorubicin) and contrast enhancing material. In exemplary embodiments, the contrast enhancing material (agent) may be, or include, any of various different types or kinds of contrast media, for example, Visipaque™ (iodixanol), or Omnipaque™ (iohexol), among many other suitable types and kinds of contrast media.

In a non-limiting manner, numerous other possible compositions and formulations of the infusion suspension, of the infusion agent, and of the infusion fluid, are applicable for implementing embodiments of the invention.

An aspect of some embodiments of the present invention relates to an embolization microcatheter for delivering an infusion agent in a small blood vessel towards a target bodily part. The microcatheter includes a single lumen surrounded by a tubular wall having an outer diameter and opened at both ends. The use of a microcatheter having a single lumen only, for delivering the infusion suspension together with disrupting retrograded flow, optionally selectively or in reaction to change is surroundings (e.g., elevation of ambient pressure above a certain degree), is advantageous, for example, for keeping the microcatheter structure as small as possible, therefore having it fit for passage through a larger-sized catheter or/and into small blood vessels.

A proximal portion of the tubular wall is connectable to a pressure source and to a reservoir configured for containing an infusion suspension of the infusion agent (e.g., including embolization material and/or contrast enhancing material, and possibly other material) in an infusion fluid, and distal portion of the tubular wall ends with a tip. The tubular wall distal portion includes an infusion agent flow disruption section applicable via the lumen and configured, when applied, to stretch from a first average diameter to a second average diameter greater than the tubular wall outer diameter when pressure inside the tubular wall distal portion equals a predetermined expansion pressure and to collapse back to the first average diameter when the pressure inside the tubular wall distal portion is less than the predetermined expansion pressure. In some embodiments, the infusion agent flow disruption section allows continuous delivery of the infusion suspension from the reservoir to the tip before, during, and after stretching or/and collapsing thereof. In some embodiments, the infusion agent flow disruption section of the microcatheter expands and collapses relative to the tubular wall outer diameter in accordance with changes of ambient pressures or/and in relation with inner pressures within the microcatheter lumen. In some embodiments, the microcatheter is particularly configured for performing local embolization in a small blood vessel, such as, for example, for feeding a cancerous target bodily part.

Referring now to the drawings, FIGS. 1A-1F schematically illustrate different side cut views representing possible scenarios of implementing exemplary embodiments of a method for performing local embolization in a small blood vessel SBV feeding a target bodily part TBP, for example, being cancerous. Target bodily part TBP may be a complete organ, or as shown, part of an organ such as organ ORG. As shown in FIG. 1A, a possible first or preliminary step may include the locating of target bodily part TBP and the small blood vessel SBV using an imaging technique (e.g., radiography, such as fluoroscopy). For example, as shown, a diagnostic catheter 10 can be introduced in a large blood vessel LBV opening to an interim blood vessel IBV interconnecting with small blood vessel SBV, having a distal opening 11 thereof oriented generally towards the proximal entry of interim blood vessel IBV.

Contrast enhancing material (agent) CM may be delivered through diagnostic catheter 10 and opening 11 into interim blood vessel IBV and small blood vessel SBV in order to facilitate effective imaging of this anatomy, allowing determination of different treatment parameters, such as a chosen route or/and positioning of an embolization microcatheter for accurately and locally occluding selectively chosen small blood vessels, or even microcirculation vessels within an entire vascular bed VB, directly feeding target bodily part TBP. In exemplary embodiments, contrast enhancing material (agent) CM may be, or include, any of various different types or kinds of contrast media, for example, Visipaque™ (iodixanol), or Omnipaque™ (iohexol), among many other suitable types and kinds of contrast media.

Figure 1B:
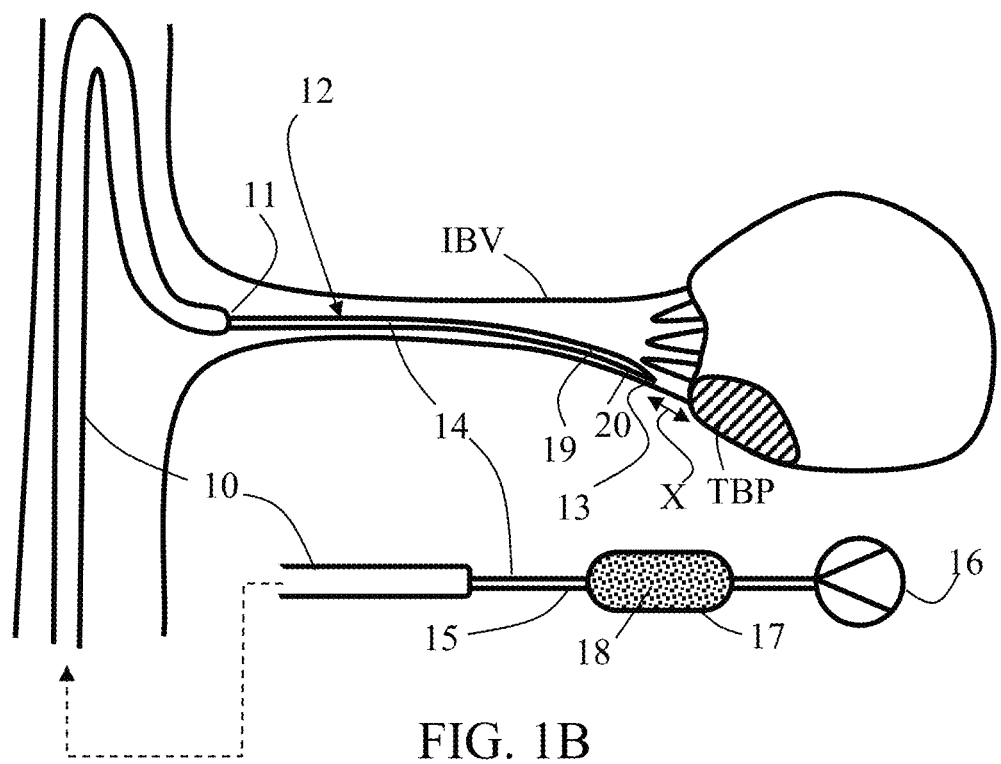

Diagnostic catheter 10, or any other catheter, may also be used for delivering the embolization microcatheter, once it is provided in approximation with the proximal entry to small blood vessel SBV. A hollow passage (not shown) opened to interim blood vessel IBV at opening 11 may have an inner diameter equal to or less than about 1 mm, as common in diagnostic catheters used in similar procedures. As shown in FIG. 1B, a microcatheter 12 is passed (through the hollow passage) into interim blood vessel IBV and small blood vessel SBV, resulting in a first average ambient pressure $P_{am1}$ in small blood vessel SBV between the distal tip of microcatheter 12 and target bodily part TBP (i.e., P(TBP) =$P_{am1}$). In exemplary embodiments, the tip including a distal outlet 13 of microcatheter 12 is positioned at a chosen distance X from target bodily part TBP.

Figure 1C:
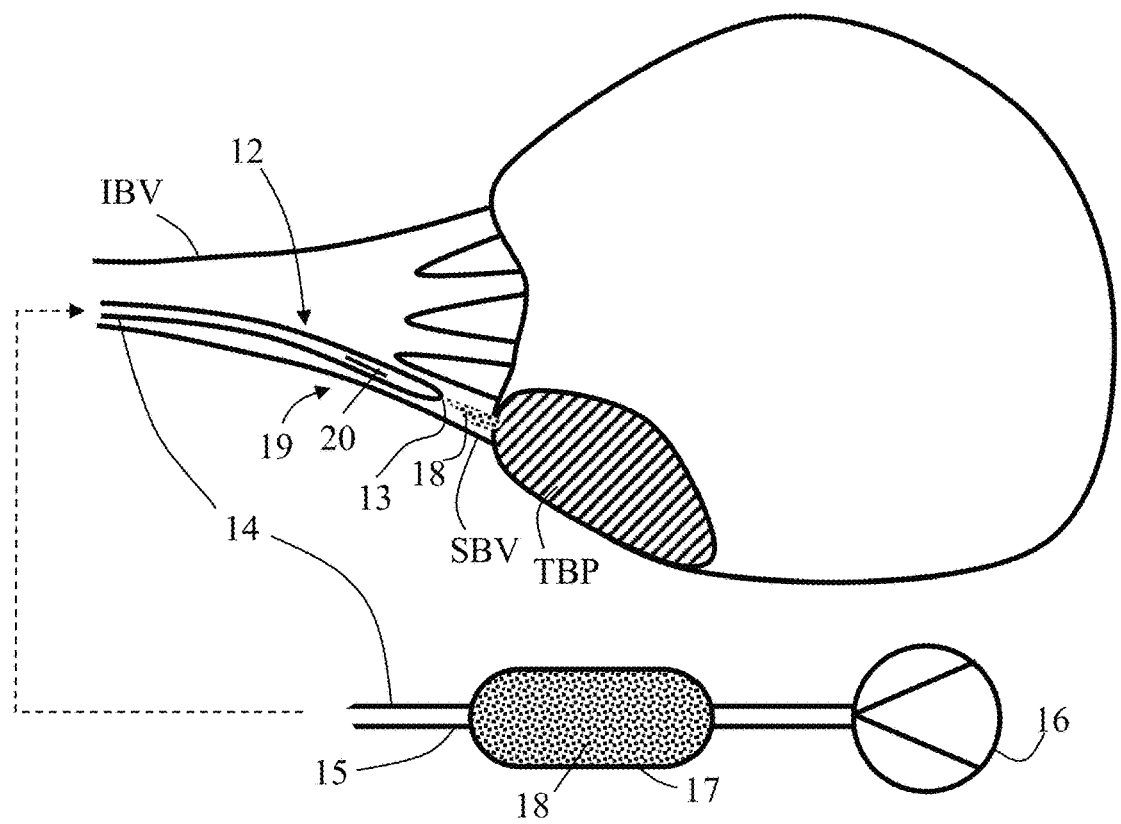

Microcatheter 12, in exemplary embodiments, includes a single lumen surrounded by a tubular wall 14 having an outer diameter and opened at both ends. A proximal portion 15 of tubular wall 14 is connectable (for example, in FIGS. 1B and 1C, shown as being connected) to a pressure source 16 and to a reservoir 17 configured for containing an infusion suspension made up of an infusion agent (e.g., embolization material and/or contrast enhancing material) 18, for example, in a form of beads. A distal portion 19 of tubular wall 14, which ends with the tip and distal outlet 13, includes an infusion agent flow disruption section 20 configured to disrupt passage of retrograded flow of the infusion agent 18 suspended in an infusion fluid (for example, being or including a contrast enhancing agent), or/and suspended in blood, flowing outside tubular wall 14 in a distal direction (i.e., in general direction from distal portion 19 towards proximal portion 15). In some embodiments, infusion agent flow disruption section 20 includes a plurality of side openings distributed around or/and along it, each opening may be shaped or/and sized to allow passage therethrough of an infusion fluid, and to block passage therethrough of the infusion agent (e.g., in a form of beads). Such openings may be in a form of pores or/and slits, or in any other relevant form or shape known in the art. In some such embodiments, delivering of infusion agent 18 through distal outlet 13 includes infusing a volume of infusion fluid through the side openings while blocking infusion agent (e.g., beads) from passing therethrough.

In exemplary embodiments, additionally or alternatively, infusion agent flow disruption section 20 is pressure sensitive and is configured to stretch or/and expand (particularly illustrated, for example, via FIG. 1E) from a first average diameter to a second average diameter greater than the tubular wall 14 outer diameter when pressure inside tubular wall distal portion 19 equals or exceeds a predetermined expansion pressure PP. In exemplary embodiments, additionally, infusion agent flow disruption section 20 is configured to collapse back to the first average diameter when the pressure inside tubular wall 14 distal portion 19 is less than the predetermined expansion pressure PP. In some embodiments, infusion agent flow disruption section 20 allows continuous delivery of infusion agent 18 from reservoir 17 to distal outlet 13—before, during, and after stretching or/and collapsing thereof.

In some embodiments, predetermined expansion pressure PP is greater than about 50 mm Hg, or greater than about 80 mm Hg, or greater than about 100 mm Hg, or greater than about 120 mm Hg, or higher, or lower, or an intermediate value.

Infusion agent 18 may include at least one of liquid embolic agents (e.g., Onyx™ by Covidien, n-butyle-2-cyanoacrylate, or ethiodized oil), sclerosing agents (e.g., ethanol, ethanolamine oleate, or sodium tetradecyl sulfate), or particulate embolic agents (e.g., hemostatic absorbable gelatin, polyvinyl alcohol (PVA), acrylic gelatin microspheres, or glass). Infusion agent 18 may include radiopaque beads or/and drug eluting beads. In exemplary embodiments, infusion agent 18 is of particulate form (e.g., nonspherical particles, or microspheres) having an average size (long dimension or diameter) in a range of between about 25 microns (μm) and about 1,500 microns (μm). In exemplary embodiments, infusion agent 18 has a compressibility in a range of between about 10% and about 40%. For example, polyvinyl alcohol (PVA) type infusion agent has a compressibility in a range of between about 20% and about 30%.

Figure 1D:
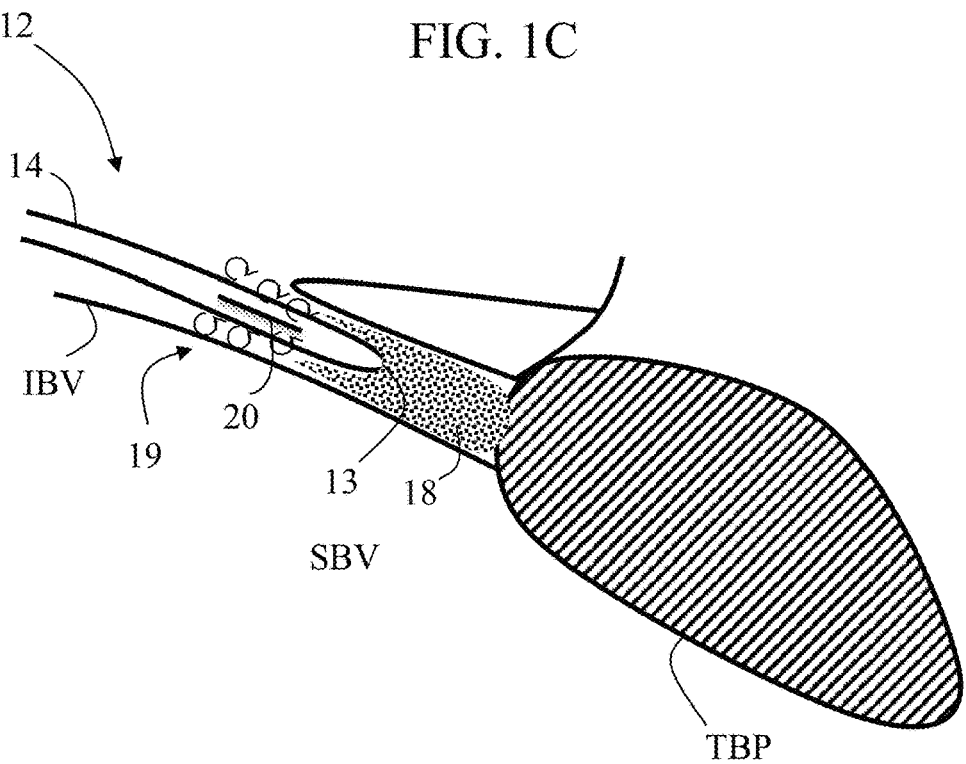

As shown in FIG. 1C, infusion agent 18 is then delivered through distal outlet 13 to target bodily part TBP. Pressure source 16 can be applied so as to generate a first inner pressure $P_{i1}$ inside tubular wall 14 distal portion 19 (i.e., P(19)=$P_{i1}$) being less than predetermined expansion pressure PP and greater than first average ambient pressure $P_{am1}$, thereby delivering an infusion suspension of infusion agent (e.g., including embolization material and/or contrast enhancing material) 18 suspended in, and carried by, an infusion (infusion agent carrier) fluid from reservoir 17 towards target bodily part TBP. Delivered infusion agent 18 may continue to accumulate between microcatheter tip and target bodily part TBP, as shown in FIG. 1D, for example as long as P(19)>P(TBP), at least until increasing pressure P(TBP) to a second greater average ambient pressure $P_{am2}$ being closer to first inner pressure $P_{i1}$. Upon elevation of the pressure P(TBP) some retrograded flow of infusion agent or/and infusion fluid or/and blood may occur. A retrograded flow of embolization material is then halted, diminished, blocked or/and interrupted by causing turbulence or vortex therein with flow disruption section 20. In some embodiments where flow disruption section 20 includes side openings, the infused volume of infusion fluid delivered in parallel or instead of infusion agent delivery through distal outlet 13 shall increases a local pressure and disrupt incoming retrograded flow of infusion agent 18.

Figure 1E:
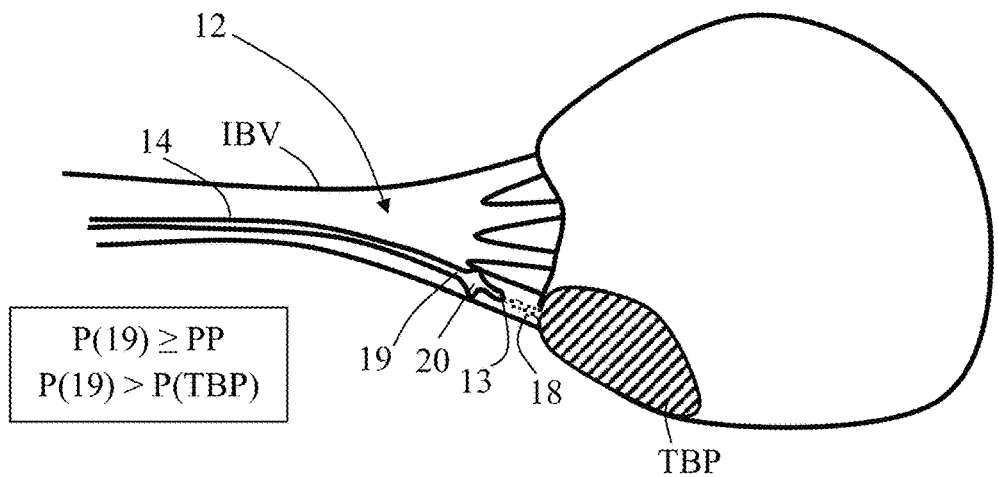

FIG. 1E shows a particular scenario in case flow disruption section 20 is activated (expanded) for disrupting retrograded flow of infusion agent (e.g., including embolization material and/or contrast enhancing material). As shown, pressurizing microcatheter lumen so as to allow distal portion pressure P(19) to become equal to or to exceed the predetermined expansion pressure PP, forces pressure sensitive section 20 to stretch until occluding small blood vessel SBV (where it may reach a maximal average diameter) or/and until reaching a selected pressure difference $P_s$ developed between tubular wall distal portion 19 and target bodily part TBP (i.e., P(TBP)−P(19)=$P_s$). In some embodiments, the maximal average diameter is equal to or larger than about 1 mm, or, equal to or higher than about 2 mm, or, equal to or higher than about 4 mm, or, equal to or higher than about 6 mm, or higher, or lower, or an intermediate value.

Figure 1F:
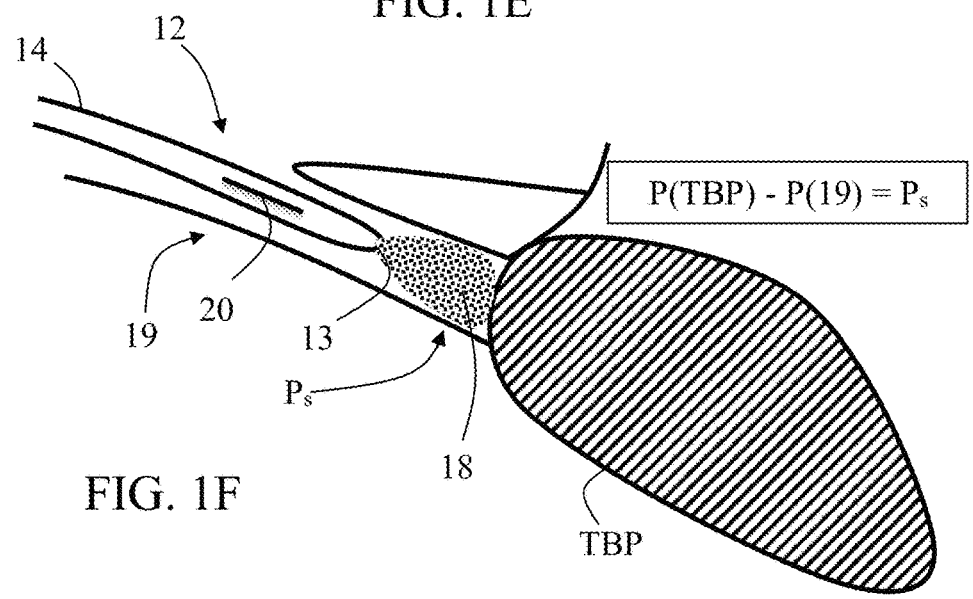
Figure 1G:
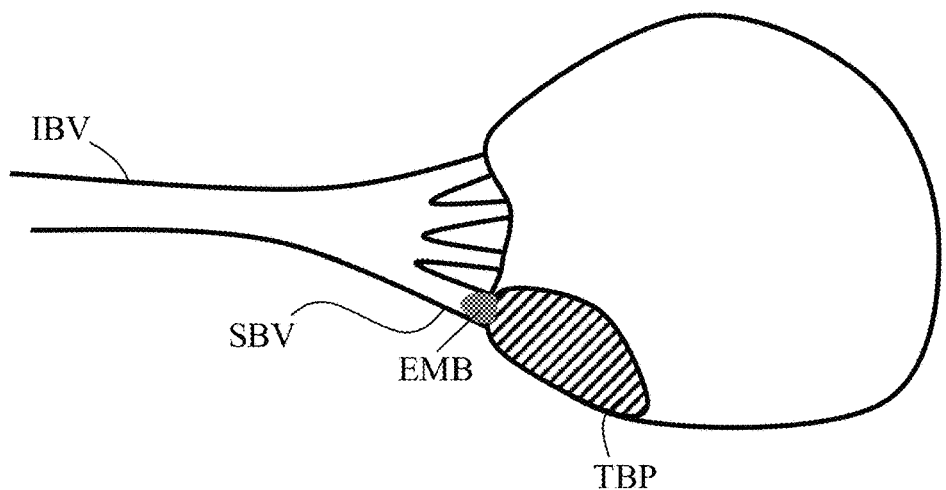

While infusion agent flow disruption section 20 may be in different sizes or forms, delivery of infusion agent 18 may continue. The selected pressure difference $P_s$ may be negative, as shown in FIG. 1F, so further delivery and accumulation of infusion agent 18 may take place as needed, while infusion agent flow disruption section 20 remains substantially collapsed. Any of the preceding steps, for example, the accumulating and pressurizing, may be repeated until forming a chosen sized embolus EMB between tip 13 and target bodily part TBP, as shown in FIG. 1G.

Figure 2A:
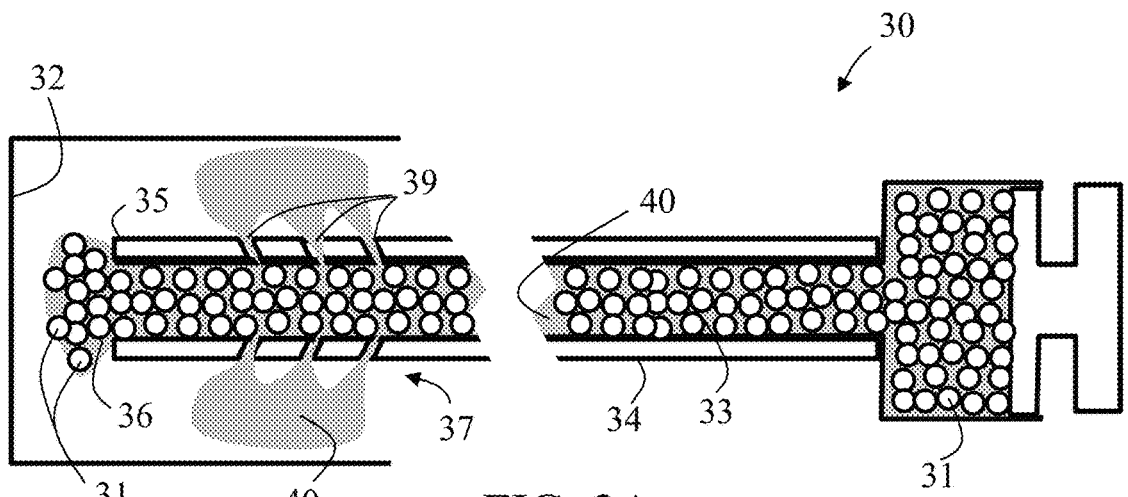
FIGS. 2A-2B are schematic side cut views of exemplary embodiments of a microcatheter during delivery of infusion agent (e.g., embolization material and/or contrast enhancing material) before (FIG. 2A) and after (FIG. 2B) occurrence of a retrograded flow, in accordance with some embodiments of the invention.
Figure 2B:
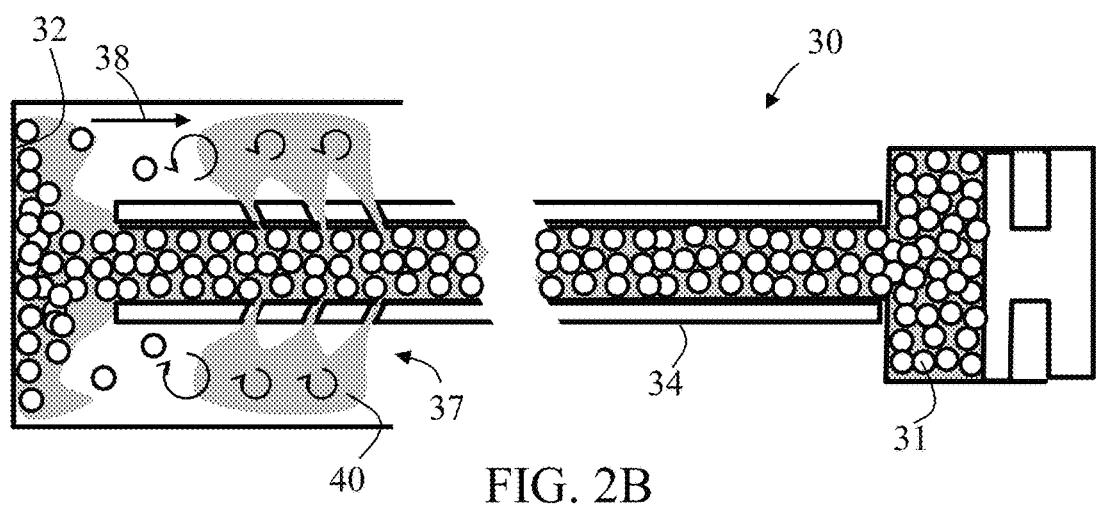

FIGS. 2A-2B schematically illustrate side cut views of exemplary embodiments of an exemplary microcatheter 30 during delivery of infusion agent 31 before (FIG. 2A) and after (FIG. 2B) occurrence of a retrograded flow. Microcatheter 30 is sized and configured for delivering infusion agent 31 in a small blood vessel towards a target bodily part 32. Microcatheter 30 includes a single lumen 33 surrounded by a tubular wall 34 having an outer diameter and opened at both ends. In some embodiments, tubular wall 34 is sized for unhindered insertion into a small blood vessel, such as a celiac or hepatic artery. In some embodiments, outer diameter of microcatheter 30 is equal to or less than about 2 mm, or equal to or less than about 1 mm. In some embodiments, microcatheter 30 has an external diameter equal to the diameter of a commercially available microcatheter, such as a 2.1 French catheter, or a 2.7 French catheter, or a 2.9 French catheter.

A proximal portion of tubular wall 34 is connectable to a pressure source and to a reservoir configured for containing an infusion suspension of an infusion agent (e.g., embolization material and/or contrast enhancing material) 31. Infusion agent 31 may include at least one of liquid embolic agents (e.g., Onyx™ by Covidien, n-butyle-2-cyanoacrylate, or ethiodized oil), sclerosing agents (e.g., ethanol, ethanolamine oleate, or sodium tetradecyl sulfate), or particulate embolic agents (e.g., hemostatic absorbable gelatin, polyvinyl alcohol (PVA), acrylic gelatin microspheres, or glass). In exemplary embodiments, infusion agent 31 is of particulate form (e.g., non-spherical particles, or microspheres) having an average size (long dimension or diameter) in a range of between about 25 microns (μm) and about 1,500 microns (μm). In exemplary embodiments, infusion agent 31 has a compressibility in a range of between about 10% and about 40%. For example, polyvinyl alcohol (PVA) type infusion agent has a compressibility in a range of between about 20% and about 30%.

A distal portion of tubular wall ends with a tip 35, enclosing a distal outlet 36. Tubular wall 34 distal portion includes an infusion agent flow disruption section 37 configured to disrupt passage of an incoming retrograded (in a general distal direction) flow 38 of the infusion agent around tubular wall 34, during continuous delivery of the infusion agent 31 from the reservoir to tip 35 and out through distal outlet 36. As shown in FIG. 2B, flow disruption section 37 is configured to diminish, or block, incoming retrograded flow 38 of the infusion agent 31, for example, thereby increasing local pressure thereabout or/and creating local turbulence or vortex. In some embodiments, the turbulence or vortex is created by infusion fluid injected or otherwise expelled from the microcatheter, for example, wherein the infusion agent 31 is partially or fully filtered from the infusion fluid.

Flow disruption section 37 includes a plurality of openings 39 distributed around or/and along it, each opening is shaped or/and sized to effect passage therethrough of an infusion fluid (such as a viscous fluid) 40, and to block passage therethrough of the infusion agent 31. In exemplary embodiments, infusion fluid 40 includes a contrast enhancing material (agent), for example, diluted to a certain degree such as with saline. In some instances, the medical practitioner may mix together a viscous contrast enhancing material (such as a contrast enhancing material or agent) with embolization material (for example, including saline and embolization beads), for example, in a volumetric ratio of 50:50, thereby producing an infusion suspension of embolization beads and contrast enhancing material or agent diluted to a chosen degree. In an exemplary embodiment, the infusion suspension includes drug-eluting beads (DEB), chemotherapeutic material (e.g., doxorubicin) and contrast enhancing material. In exemplary embodiments, the contrast enhancing material (agent) (such as contrast enhancing material (agent) CM shown in FIG. 1A) may be, or include, any of various different types or kinds of contrast media, for example, Visipaque™ (iodixanol), or Omnipaque™ (iohexol), among many other suitable types and kinds of contrast media.

One or more opening 39 includes a pore having a cross sectional dimension less than minimal diameter of the infusion agent, for example, embolization material (e.g., bead diameter). Such cross sectional dimension is, for example, less than about 500 microns (μm), or, equal to or less than about 100 microns (μm), or, equal to or less than about 40 microns (μm). In exemplary embodiments, the cross section dimension is in a range of between about 20 microns (μm) and about 30 microns (μm), for example, about 28 microns (μm). For example, as shown, each pore is located at end of a channel being angled (wherein the angle is an exemplary range of between about 0 degrees and about 90 degrees) relative to a long axis of lumen 33 or/and relative to a radial axis thereof at a cross section adjacent thereto. In exemplary embodiments, at least two pores are angularly located in different directions such that a first stream of the infusion suspension in immediate vicinity of a first pore at least partially intersects a second stream of the infusion suspension in immediate vicinity of a second pore. Openings 39 or pores may be in any possible form, for example, with circular or rectangular cross section, or as a burst slit (i.e., opened only under chosen pressure or force), or a constantly opened slit. In such exemplary embodiments, the openings 39 or pores have a minimal cross sectional dimension being less than the minimal diameter of the infusion agent (e.g., embolization material, (for example, in the form of beads).

In some embodiments, lumen 33 is configured to deliver a suspension of infusion fluid 40 and infusion agent 31, for example, in a form of beads. In some embodiments, distal outlet 36 is shaped or/and sized to effect passage therethrough of the infusion suspension of infusion fluid 40 and the infusion agent (beads) 31, and at least one side opening 39 is shaped or/and sized to effect passage therethrough of infusion fluid 40, and to block passage therethrough of infusion agent (beads) 31, for example, if a cross sectional dimension of the pore in each opening is less than a minimal diameter of the infusion agent (beads).

In some embodiments, at least one side opening 39 is shaped or/and sized to effect passage therethrough of infusion fluid 40, and to block passage therethrough of infusion agent (beads) 31, during flow of the infusion suspension through distal outlet 36. In some other embodiments, at least one side opening 39 is shaped or/and sized to effect passage therethrough of infusion fluid 40, and to block passage therethrough of infusion agent (beads) 31, during conditions when the infusion suspension is blocked or interrupted from flowing through distal outlet 36.

In some embodiments, a total opened cross section of all openings 39 is equal to or greater than a smallest cross section of lumen 33 and distal outlet 36.

In some embodiments, infusion fluid 40 at normal body temperature has an average viscosity of at least about 0.8 mPa·s, or at least about 5 mPa·s, or at least about 10 mPa·s, or at least about 20 mPa·s. In exemplary embodiments, infusion fluid 40 is pre-heated, for example, to a temperature higher than about 37° C., before reaching tubular wall 34 distal portion in lumen 33. In exemplary embodiments, infusion fluid 40 includes, or is mixed with, another infusable fluid (e.g., glucose water), for example, also pre-heated with infusion fluid 40 or separately pre-heated.

In some embodiments, a farthest distal side opening 39 is located within a range of between about 0 mm and about 20 mm, or within a range of between about 0 mm and about 10 mm, or within a range of between about 0 mm and about 5 mm, proximally to distal outlet 36.

Figure 3:
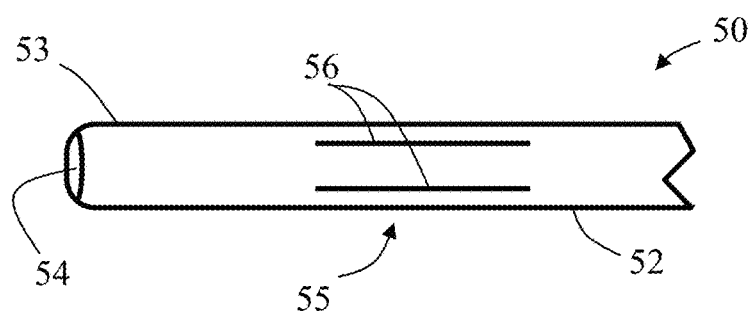
FIG. 3 is a schematic top view of an exemplary embodiment of an infusion agent flow disruption section having openings in form of slits, in accordance with some embodiments of the invention.

FIG. 3 schematically illustrates a top view of an exemplary embodiment of an infusion agent flow disruption section 55 (included in an exemplary microcatheter 50) having openings in form of slits. Microcatheter 50 is sized and configured for delivering infusion agent, for example, including embolization material (e.g., in a form of beads) in a small blood vessel, towards a target bodily part. Microcatheter 50 includes a tubular wall 52 having a distal portion which ends with a tip 53, enclosing a distal outlet 54. Tubular wall 52 distal portion includes an infusion agent flow disruption section 55 configured to disrupt passage therethrough of an incoming retrograded flow of the infusion agent, for example, during continuous delivery of the infusion agent through distal outlet 54. Flow disruption section 55 is configured to block, or/and cause turbulence in, incoming retrograded flow of the infusion agent, thereby increasing local pressure thereabout.

Flow disruption section 55 includes a plurality of openings 56 distributed around or/and along it, each opening includes a slit with a gap having a cross sectional dimension (e.g., width) less than minimal diameter of the infusion agent. In exemplary embodiments, another cross sectional dimension of this gap (e.g., length) is substantially greater than the minimal diameter of the infusion agent. In some embodiments, each opening is shaped or/and sized to effect passage therethrough of an infusion fluid, and to block passage therethrough of the infusion agent.

In some embodiments, flow disruption section 55 includes material being firmer than material of other sections of tubular wall 52 distal portion. In exemplary embodiments, flow disruption section 55 is made of a metallic material, a hard polymeric material, or a combination thereof. In exemplary embodiments, flow disruption section 55 is coated with a radiopaque material such as with hydrophilic coating. In exemplary embodiments, flow disruption section 55 is structured with a metal coil, for example, impregnated with solid structure or/and attached to a layer of solid structure.

Figure 4A:
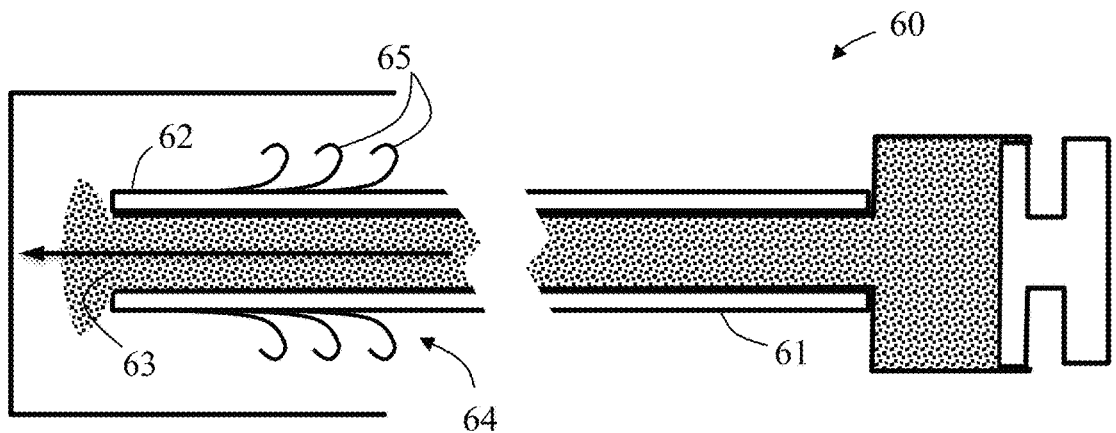
FIGS. 4A-4B are schematic side cut views of exemplary embodiment of a microcatheter including a plurality of projections, during delivery of infusion agent (e.g., embolization material and/or contrast enhancing material) before (FIG. 4A) and after (FIG. 4B) occurrence of a retrograded flow, in accordance with some embodiments of the invention.
Figure 4B:
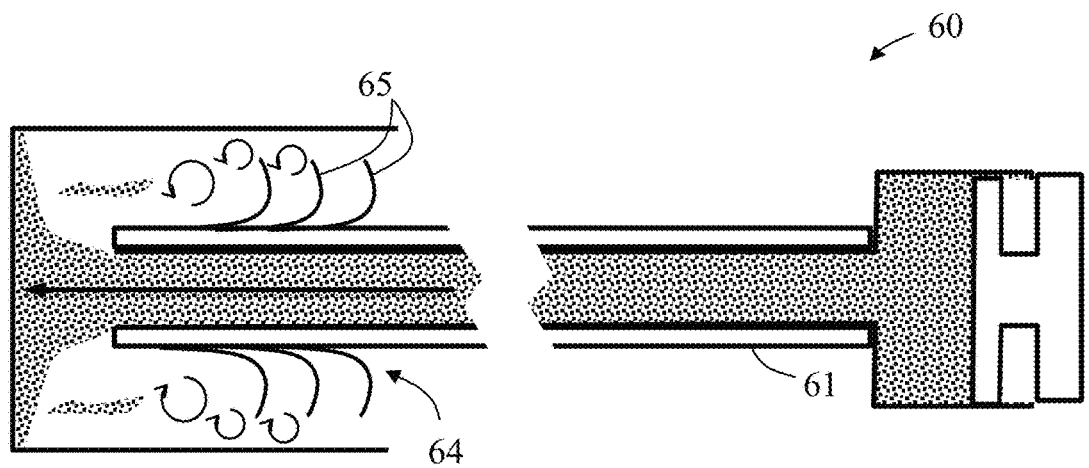

FIGS. 4A-4B schematically illustrate side cut views of exemplary embodiments of a microcatheter 60 including a plurality of projections, during delivery of infusion agent (e.g., embolization material) before (FIG. 4A) and after (FIG. 4B) occurrence of a retrograded flow. Microcatheter 60 is sized and configured for delivering the infusion agent, for example, embolization material (e.g., in a form of beads) in a small blood vessel, towards a target bodily part. Microcatheter 60 includes a tubular wall 61 having a distal portion which ends with a tip 62, enclosing a distal outlet 63. In some embodiments, tubular wall 61 is sized for unhindered insertion into a small blood vessel, such as a celiac or hepatic artery. In some embodiments, outer diameter of microcatheter 60 is equal to or less than about 2 mm, or equal to or less than about 1 mm. In some embodiments, microcatheter 60 has an external diameter equal to the diameter of a commercially available microcatheter, such as a 2.1 French catheter, a 2.7 French catheter, or a 2.9 French catheter.

Tubular wall 61 distal portion includes an infusion agent flow disruption section 64 configured to disrupt passage of an incoming retrograded flow of the infusion agent, during continuous delivery of the infusion agent through distal outlet 63. Flow disruption section 64 is configured to diminish, block, or/and cause turbulence or vortex in, incoming retrograded flow of the infusion agent in a distal direction around Tubular wall 61 distal portion adjacent thereto, and optionally increase local pressure thereabout.

Flow disruption section 64 includes a plurality of projections 65 branching out from and distributed around or/and along it. In exemplary embodiments, projections 65 are flexible or/and configured to bend proximally into a straight form along tubular wall 61 distal portion when flow disruption section 64 is passed distally within a closely fitting outer tube. In exemplary embodiments, projections 65 are curled distally towards tip 62 when in a relaxed configuration such as in absence of retrograded flow.

Figure 5A:
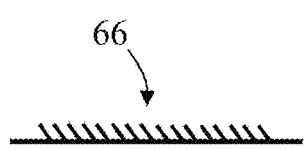
FIGS. 5A-5D are schematic partial side cut views of exemplary embodiments of different exemplary projections of an infusion agent flow disruption section, in accordance with some embodiments of the invention.
Figure 5B:
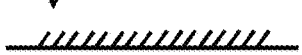
Figure 5C:
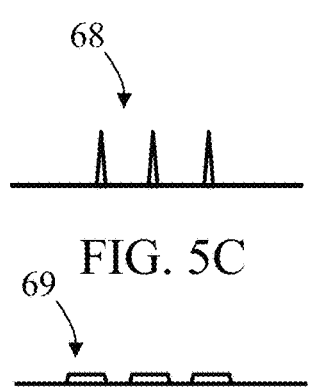
Figure 5D:

FIGS. 5A-5D schematically illustrate partial side cut views of exemplary embodiments of different exemplary projections of an infusion agent flow disruption section. FIG. 5A shows projections 66 in a form of threads angled distally at least when in relaxed configuration, FIG. 5B shows projections 67 in a form of threads angled proximally at least when in relaxed configuration, FIG. 5C shows projections 68 in a form of prongs, and FIG. 5D shows projections 69 in a form of bulges, for example, as a result of a coil wounded over the low disruption section.

Reference is now made to FIGS. 6A-6D, which schematically illustrate side cut views of exemplary embodiments of a microcatheter 70 in different scenarios, particularly highlighting an exemplary infusion agent flow disruption section included in the microcatheter tubular wall distal portion. Microcatheter 70 includes a single lumen 71 surrounded by a tubular wall 72 having an outer diameter 73 and opened at both ends. In some embodiments, tubular wall 72 is sized for unhindered insertion into a small blood vessel 73, such as a celiac or hepatic artery. In some embodiments, outer diameter 73 is equal to or less than about 2 mm, or, equal to or less than about 1 mm. In some embodiments, microcatheter 70 has an external diameter equal to the diameter of a commercially available microcatheter, such as a 2.1 French catheter, a 2.7 French catheter, or a 2.9 French catheter.

In some embodiments, tubular wall 72 is configured for delivering a suspension of infusion agent (e.g., embolization material and/or contrast enhancing material) in an infusion fluid to a target bodily part such as a tumor or cancerous tissue. A proximal portion 74 of tubular wall 72 is connectable to a pressure source 75 and to a reservoir 76 configured for containing the suspension of the infusion agent (e.g., embolization material) 77. Infusion agent 77 may include at least one of liquid embolic agents (e.g., Onyx™ by Covidien, n-butyle-2-cyanoacrylate, or ethiodized oil), sclerosing agents (e.g., ethanol, ethanolamine oleate, or sodium tetradecyl sulfate), or particulate embolic agents (e.g., hemostatic absorbable gelatin, polyvinyl alcohol, or acrylic gelatin microspheres).

Figure 6A:
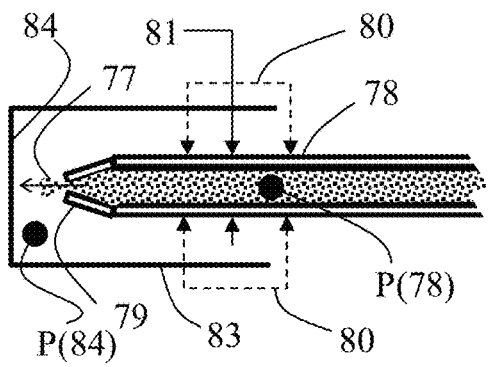
FIGS. 6A-6D are schematic side cut views of exemplary embodiments of a microcatheter in different scenarios, particularly highlighting an exemplary infusion agent flow disruption section included in the microcatheter tubular wall distal portion, in accordance with some embodiments of the invention.
Figure 6A:
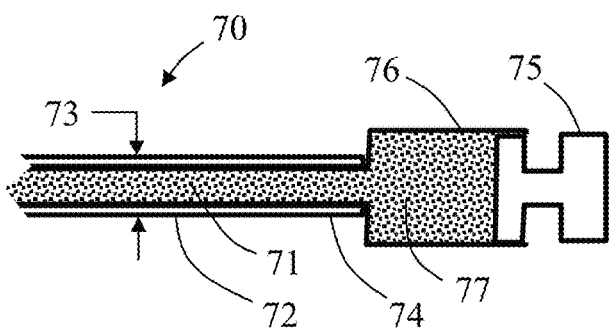
Figure 6B:
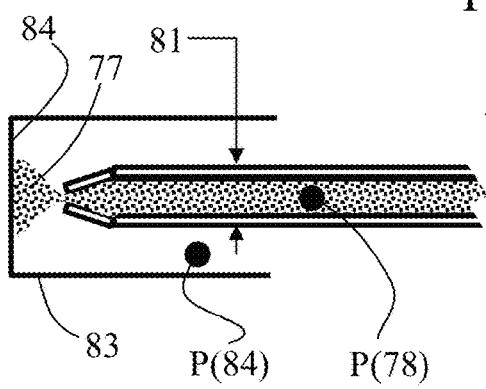
Figure 6B:
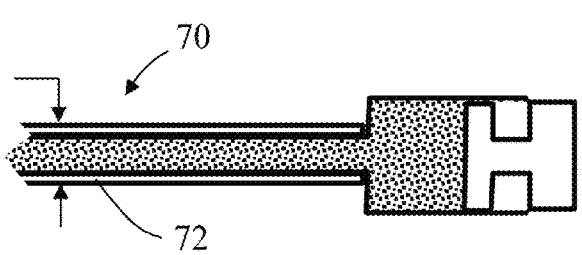
Figure 6C:
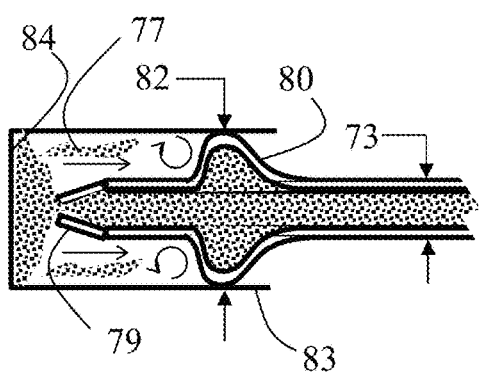
Figure 6C:
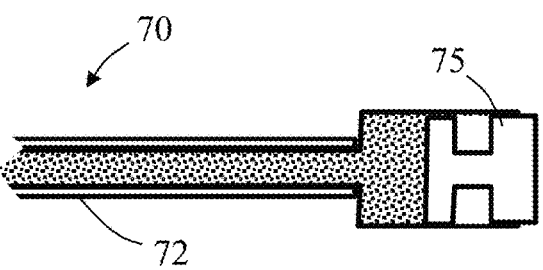
Figure 6D:
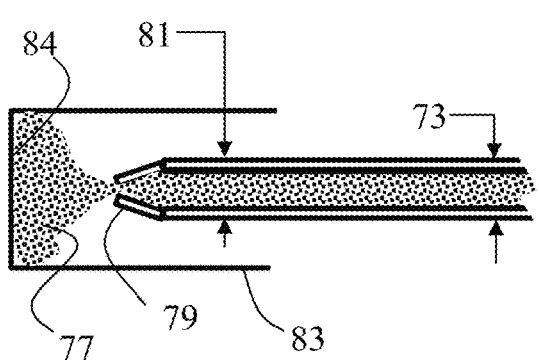

Distal portion 78 includes an infusion agent flow disruption section 80 configured to stretch from a first average diameter 81 (as shown in FIGS. 6A, 6B, and 6D) to a second average diameter, for example, up to a maximal average diameter 82 (FIG. 6C), greater than tubular wall 72 outer diameter 73, when pressure P(78) inside the tubular wall 72 distal portion 78 equals or exceeds a predetermined expansion pressure Pdt. In some embodiments, predetermined expansion pressure Pdt is greater than about 50 mm Hg, or greater than about 80 mm Hg, or greater than about 100 mm Hg, or greater than about 120 mm Hg, or higher, or lower, or an intermediate value. In some embodiments, maximal average diameter 82 is equal to or higher than about 1 mm, or, equal to or higher than about 2 mm, or, equal to or higher than about 4 mm, or, equal to or higher than about 6 mm, or higher, or lower, or an intermediate value.

In some embodiments, other portions of tubular wall 72 are not subject for inflation under applicable pressures in intra-body procedures, although in other embodiments, other infusion agent flow disruption sections may be provided along or/and around tubular wall 72, having similar or different expansion and sensitivity parameters to infusion agent flow disruption section 80. In exemplary embodiments, infusion agent flow disruption section 80 is further configured to collapse back to first average diameter 81 when pressure P(78) is less than predetermined expansion pressure Pdt. In exemplary embodiments, first average diameter 81 substantially equals outer diameter 73 (as shown), or is smaller therefrom.

A distal portion 78 of tubular wall 72 ends with a tip 79. In exemplary embodiments, tip 79 is configured for suppressing flow rate in a distal direction or/and to increase locally the pressure P(78) in distal portion 78, distally to infusion agent flow disruption section 80. Tip 79 may be shaped (e.g., narrowed, for example, gradually, as shown, or as an orifice), accordingly, for this purpose. In exemplary embodiments, tip 79 is configured to maintain a pressure difference between internal pressure P(78) and surrounding pressure P(84), at least within a chosen range of pressure P(78). In some embodiments, a relief mechanism, for example, a burst opening (e.g., burst slit), may be provided with microcatheter 70, for example, adjacent to tip 79 or/and to infusion agent flow disruption section 80 for allowing immediate pressure drop in case the pressure P(78) in distal portion 78 increases above a maximally allowed value.

In some embodiments, infusion agent flow disruption section 80 allows continuous delivery of infusion agent 77 from reservoir 76 to tip 79 before, during, or/and after stretching or/and collapsing thereof.

In some embodiments, infusion agent flow disruption section 80 includes an outer wall made of material(s), for example, being thinner or/and more flexible than material(s) of other wall portions of tubular wall 72. Materials may be of different types, including metals, plastics, resilient materials, elastic material, super-elastic material, or rigid materials. In some embodiments, microcatheter 70 is configured as a single integrated structure, wherein tubular wall 72 includes, and is structurally continuous with, infusion agent flow disruption section 80 as a single member. In alternative embodiments, infusion agent flow disruption section 80 is made, at least partially, as a separate part, and later assembled with the entire outer wall 72 to form a single microcatheter body.

In some embodiments, tubular wall 72 is configured for delivery of an infusion suspension of an infusion agent (e.g., embolization material and/or contrast enhancing material) 77 from reservoir 76 thru lumen 71 and tip 79 towards a target bodily part (represented in this example by wall 84) in direct blood communication with small blood vessel 83. Infusion agent delivery occurs when internal pressure P(78) inside tubular wall 72 distal portion 78 is less than predetermined expansion pressure Pdt and greater than a first average ambient pressure developed between tubular wall 72 distal portion 78 and target bodily part/wall 84 upon inserting tubular wall 72 in small blood vessel 83.

The infusion agent flow disruption section 80 is configured such that upon elevation to a second average ambient pressure within small blood vessel 83, being equal to or greater than initial internal pressure P(78), upon accumulation of infusion agent 77 between tip 79 and target bodily part/wall 84, the pressure P(78) is increasable to a second inner pressure being equal to or greater than predetermined expansion pressure Ptd, whereby the infusion agent flow disruption section 80 stretches to the second average diameter. In some embodiments, stretching stops after occluding small blood vessel 83 or/and until a selected pressure difference P(S) is developed between tubular wall distal portion 78 and target bodily part/wall 84. In some embodiments, microcatheter 70 is configured such that, under a selected third inner pressure being greater than the first inner pressure and less than the second inner pressure, infusion agent flow disruption section 80 stretches in response to a systole and collapses in response to a diastole, relative to the second average ambient pressure.

In some embodiments, infusion agent flow disruption section 80 is configured to expand from first average diameter 81 to a maximal second average diameter greater than inner diameter of small blood vessel 83. In alternative embodiments, infusion agent flow disruption section 80 is configured to expand to a maximal second average diameter less than inner diameter of small blood vessel 83.

In some embodiments, as shown in FIG. 6C, infusion agent flow disruption section 80 is shaped, once expanded to maximal average diameter 82 or/and to a diameter sized between outer diameter 73 and maximal average diameter 82, to induce turbulent flow in distal approximation thereto upon flowing (e.g., via back flowing) of infusion agent 77 away from target bodily part 84 and towards tip 79.

In some embodiments, infusion agent flow disruption section is made from material being the same as that of the rest of tubular wall 72. In exemplary embodiments, infusion agent flow disruption section 80 is made of a material being impermeable to infusion agent 77, such that when infusion agent flow disruption section 80 stretches to a second average diameter, the impermeable material prevents passage and flowing (e.g., via back flowing) of the infusion agent 77 therethrough.

FIG. 6A shows microcatheter 70 at initial stages of infusion agent delivery, when the pressure difference P(84)–P(78) is negative while pressure P(78) in distal portion 78 is substantially lower than predetermined expansion pressure Pdt. FIG. 6B shows microcatheter 70 at a higher pressure P(78) in distal portion 78, yet still below predetermined expansion pressure Pdt, therefore although the pressure difference may either be negative but small in magnitude, null, or even positive, the infusion agent flow disruption section 80 may still maintain the first average diameter 81. In FIG. 6C, pressure difference P(84)–P(78) is positive while pressure source 75 elevates pressure P(78) to exceed predetermined expansion pressure Pdt in a magnitude that causes infusion agent flow disruption section 80 to stretch to maximal average diameter 82, preventing infusion agent 77 back flowing therethrough, for example, while causing local turbulences which may decrease pressure difference P(84)–P(78). FIG. 6D shows microcatheter 70 under a selected pressure difference P(S) where pressure P(78) in distal portion 78 is less than predetermined expansion pressure Pdt, therefore infusion agent flow disruption section 80 collapses back to first average diameter 81.

In some embodiments, microcatheter 70 may be used in a method for performing local embolization in a small blood vessel feeding a cancerous target bodily part. In some embodiments. In exemplary embodiments, the method may include at least one of the following steps (not necessarily in same order).

Providing an embolization microcatheter, for example, microcatheter 70, including a tubular wall having an outer diameter, enclosing a single lumen extending therealong, and including a distal portion ending with a tip opened to the lumen with a distal outlet, the tubular wall distal portion includes an infusion agent flow disruption section applicable via the lumen and configured to disrupt passage around periphery of the distal portion of an incoming retrograded flow of infusion agent, during a continuous delivery of an infusion suspension of the infusion agent in an infusion fluid through the lumen to the tip.

Locating the target bodily part and the small blood vessel using an imaging technique.

Providing a catheter in close proximity to a proximal entry to the small blood vessel, the catheter includes a hollow passage opened to the small blood vessel and has an inner diameter equal to or less than 1 mm.

Passing microcatheter 70 through the hollow passage and into the small blood vessel until tip 79 is in a chosen distance from the target bodily part.

Applying pressure source 75, thereby delivering infusion agent (e.g., embolization material and/or contrast enhancing material) 77 from reservoir 76 to the target bodily part.

Accumulating infusion agent 77 between the microcatheter tip 79 and the target bodily part.

Pressurizing lumen 71 so as to allow the pressure P(78) inside tubular wall distal portion 78 to become equal to or exceed the predetermined expansion pressure Pdt, whereby infusion agent flow disruption section 80 stretches until occluding the small blood vessel or/and until a selected pressure difference P(S) is developed between the tubular wall distal portion and the target bodily part.

Figure 7A:
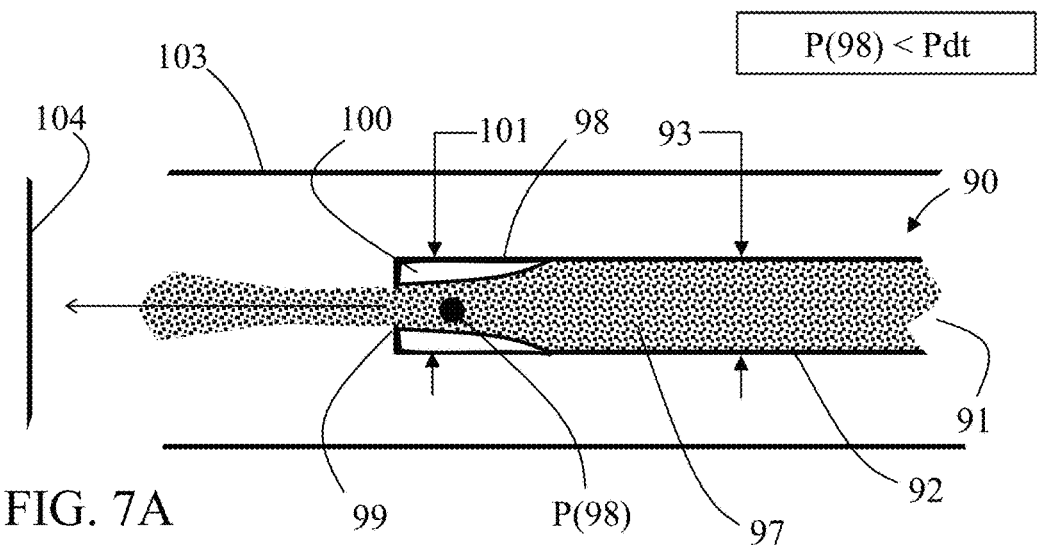
FIGS. 7A-7C are schematic side cut views of exemplary embodiments of a microcatheter in different scenarios, particularly highlighting an exemplary infusion agent flow disruption section included in the microcatheter tubular wall distal portion, in accordance with some embodiments of the invention.
Figure 7B:
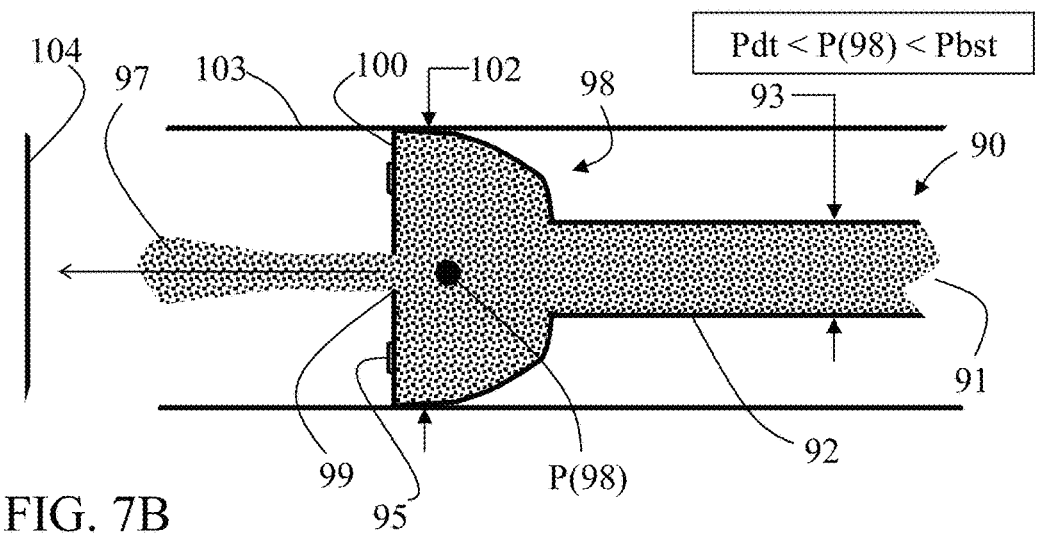
Figure 7C:
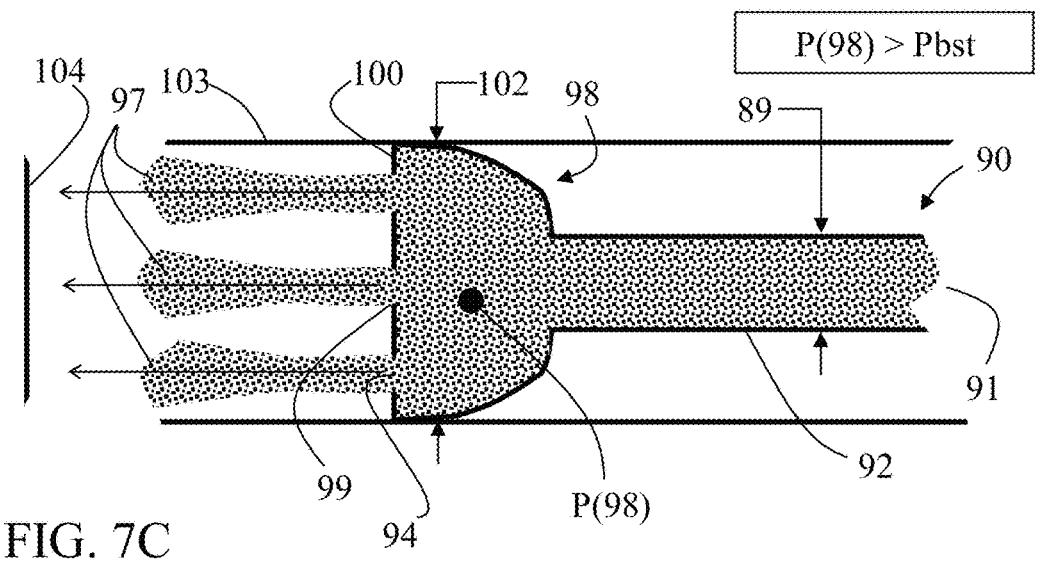

Reference is now made to FIGS. 7A-7C, which schematically illustrate side cut views of exemplary embodiments of a microcatheter 90 in different scenarios, particularly highlighting an exemplary infusion agent flow disruption section included in the microcatheter tubular wall distal portion. Microcatheter 90 includes a single lumen 91 surrounded by a tubular wall 92 having an outer diameter 93 and opened at both ends. In some embodiments, tubular wall 92 is sized for unhindered insertion into a small blood vessel 103, such as a celiac or hepatic artery. In some embodiments, outer diameter 93 is equal to or less than about 2 mm, or, equal to or less than about 1 mm. In some embodiments, microcatheter 90 is measured as a 2.7 French catheter.

In some embodiments, tubular wall 92 is configured for delivering infusion agent to a target bodily part such as a tumor or cancerous tissue. A proximal portion of tubular wall 92 is connectable to a reservoir and a pressure source (for example, as shown in FIGS. 1B, 10, 2A-2D) configured for containment and delivery of infusion agent 97. Infusion agent 97 may include at least one of liquid embolic agents (e.g., Onyx™ by Covidien, n-butyle-2-cyanoacrylate, or ethiodized oil), sclerosing agents (e.g., ethanol, ethanolamine oleate, or sodium tetradecyl sulfate), or particulate embolic agents (e.g., hemostatic absorbable gelatin, polyvinyl alcohol, or acrylic gelatin microspheres).

Distal portion 98 includes an infusion agent flow disruption section 100 configured to stretch from a first average diameter 101 (FIG. 7A) to a second average diameter, for example, up to a maximal average diameter 102 (FIGS. 7B and 7C), greater than tubular wall 92 outer diameter 93, when pressure P(98) inside the tubular wall 92 distal portion 98 equals or exceeds a predetermined expansion pressure Pdt. In some embodiments, predetermined expansion pressure Pdt is greater than about 50 mm Hg, or greater than about 80 mm Hg, or greater than about 100 mm Hg, or greater than about 120 mm Hg, or higher, or lower, or an intermediate value. In some embodiments, maximal average diameter 102 is equal to or greater than about 1 mm, or, equal to or greater than about 2 mm, or, equal to or greater than 4 mm, or, equal to or greater than about 6 mm, or higher, or lower, or an intermediate value. In some embodiments, other portions of tubular wall 92 are not subject for inflation under applicable pressures in intra-body procedures, although in other embodiments, other infusion agent flow disruption sections may be provided along or/and around tubular wall 92, having similar or different expansion and sensitivity parameters to infusion agent flow disruption section 100. In exemplary embodiments, infusion agent flow disruption section 100 is further configured to collapse back to first average diameter 101 when pressure P(98) is less than predetermined expansion pressure Pdt. In exemplary embodiments, first average diameter 101 substantially equals outer diameter 93 (as shown), or, is smaller or greater therefrom.

A distal portion 98 of tubular wall 92 ends with a tip 99. In exemplary embodiments, tip 99 is shaped (e.g., narrowed) in order to maintain a pressure difference between internal pressure P(98) and surrounding pressure P(104), at least within a chosen range of pressure P(98). In some embodiments, and as shown, infusion agent flow disruption section 100 includes tip 99.

In some embodiments, a relief mechanism (for example, a burst opening for expelling fluid) may be provided with microcatheter 90, for example, adjacent to tip 99 or/and to infusion agent flow disruption section 100, for allowing immediate pressure drop in case the pressure P(98) in distal portion 98 increases above a maximally allowed value. In some embodiments, and as shown in FIG. 7C, infusion agent flow disruption section 100 includes a sub-section having at least one opening, for example, opening 94, sized to allow passage therethrough of infusion agent 97 when infusion agent flow disruption section 100 is at least partially stretched, or, for example, after infusion agent flow disruption section 100 is fully stretched. Infusion agent flow disruption section 100 may be configured such that the at least one opening 94 is obstructed (such as by covering or elastic closure 95, shown in FIG. 7B) to prevent infusion agent 97 flowing therethrough when infusion agent flow disruption section 100 is at first average diameter 101, or, for example, at greater diameter, such as maximal average diameter 102, yet below a predetermined burst pressure Pbst. In exemplary embodiments, burst pressure Pbst is substantially higher than predetermined expansion pressure Pdt, for example, by at least about 20 mm Hg, or by at least about 50 mm Hg, or higher, or lower, or an intermediate value. In some embodiments, and as shown in FIG. 7C, infusion agent flow disruption section 100 is configured such that the at least one opening 94 is directed at least partially in a distal direction of tubular wall 92 or/and towards tip 99, at least when opened (i.e., unobstructed).

In some embodiments, infusion agent flow disruption section 100 allows continuous delivery of infusion agent 97 from the reservoir to tip 99 before, during, or/and after stretching or/and collapsing thereof. In some such embodiments, when portion openings 94 are unobstructed, infusion agent 97 can be delivered therethrough in parallel to delivery thru tip 99.

In some embodiments, infusion agent flow disruption section 100 includes an outer wall, for example, thinner or/and more flexible than other wall portions of tubular wall 92. In some embodiments, microcatheter 90 is configured as a single integrated structure, wherein tubular wall 92 includes, and is structurally continuous with, infusion agent flow disruption section 100 as a single member. In alternative embodiments, infusion agent flow disruption section 100 is made, at least partially, as a separate part, and later assembled with the entire outer wall 92 to form a single microcatheter body.

In some embodiments, tubular wall 92 is configured for delivery of infusion agent 97 from a reservoir thru lumen 91 and tip 99 (and, for example, thru the at least one opening 94) towards a target bodily part (represented in this example by wall 104) in direct blood communication with small blood vessel 103. Infusion agent delivery occurs when internal pressure P(98) inside tubular wall 92 distal portion 98 is less than predetermined expansion pressure Pdt and greater than a first average ambient pressure developed between tubular wall 92 distal portion 98 and target bodily part/wall 104 upon inserting tubular wall 92 in small blood vessel 103.

The infusion agent flow disruption section 100 is configured such that upon elevation to a second average ambient pressure within small blood vessel 103, being equal to or greater than initial internal pressure P(98), upon accumulation of infusion agent 97 between tip 99 and target bodily part/wall 104, the pressure P(98) is increasable to a second inner pressure being equal to or greater than predetermined expansion pressure Pdt, whereby infusion agent flow disruption section 100 stretches (for example, as shown in FIG. 7B). In some embodiments, stretching stops after occluding small blood vessel 103 or/and until a selected pressure difference is developed between tubular wall distal portion 98 and target bodily part/wall 104. In some embodiments, microcatheter 90 is configured such that, under a selected third inner pressure being greater than the first inner pressure and less than the second inner pressure, infusion agent flow disruption section 100 stretches in response to a systole and collapses in response to a diastole, relative to the second average ambient pressure.

In some embodiments, infusion agent flow disruption section 100 is configured to expand from first average diameter 101 to a maximal second average diameter greater than inner diameter of small blood vessel 103. In alternative embodiments, infusion agent flow disruption section 100 is configured to expand to a maximal second average diameter less than inner diameter of small blood vessel 103.

In some embodiments, infusion agent flow disruption section 100 is shaped, once expanded to maximal average diameter 102 or/and to a diameter sized between outer diameter 93 and maximal average diameter 102, to induce turbulent flow in distal approximation thereto upon flowing (e.g., via back flowing) of infusion agent 97 away from target bodily part 104 and towards tip 99.

FIGS. 8A-8B schematically illustrate partial side cut views of exemplary embodiments of a portion of an infusion agent flow disruption section 111 (in exemplary microcatheter 110) that includes a valve mechanism 112, before (FIG. 8A) and after (FIG. 8B) actuation thereof. Microcatheter 110 may be an embolization microcatheter sized and configured for delivering infusion agent (e.g., embolization material and/or contrast enhancing material) 113 (e.g., in the form of beads) in a small blood vessel towards a target bodily part. Microcatheter 110 includes a lumen 114 surrounded by a tubular wall 115 having an outer diameter and opened at both ends. In some embodiments, tubular wall 115 is sized for unhindered insertion into a small blood vessel, such as a celiac or hepatic artery. In some embodiments, outer diameter of microcatheter 110 is equal to or less than about 2 mm, or, equal to or less than about 1 mm. In some embodiments, microcatheter 110 has an external diameter equal to the diameter of a commercially available microcatheter, such as a 2.1 French catheter, a 2.7 French catheter, or a 2.9 French catheter.

Infusion agent 113 may include at least one of liquid embolic agents (e.g., Onyx™ by Covidien, n-butyle-2-cyanoacrylate, or ethiodized oil), sclerosing agents (e.g., ethanol, ethanolamine oleate, or sodium tetradecyl sulfate), or particulate embolic agents (e.g., hemostatic absorbable gelatin, polyvinyl alcohol (PVA), acrylic gelatin microspheres, or glass). In exemplary embodiments, infusion agent 113 is of particulate form (e.g., non-spherical particles, or microspheres) having an average size (long dimension or diameter) in a range of between about 25 microns (μm) and about 1,500 microns (μ). In exemplary embodiments, infusion agent 113 has a compressibility in a range of between about 10% and about 40%. For example, polyvinyl alcohol (PVA) type infusion agent has a compressibility in a range of between about 20% and about 30%.

Infusion agent flow disruption section 111 is configured to disrupt passage of an incoming retrograded flow 119 of the infusion agent around outer periphery of tubular wall 115 distal end adjacent thereto, during continuous delivery of infusion agent 113 through distal outlet of microcatheter 110. Flow disruption section 111 is configured to diminish, block, or/and cause turbulence or vortex in, incoming retrograded flow 119 of the infusion agent, optionally increasing local pressure thereabout.

Flow disruption section 111 includes a plurality of (side) openings 116 distributed around or/and along it, each opening is shaped or/and sized to allow passage therethrough of an infusion fluid 117, and to block passage therethrough of the infusion agent 113.

Infusion fluid 117, in exemplary embodiments, includes a contrast enhancing agent, for example, diluted to a certain degree such as by saline. In some instances, the medical practitioner may mix together a viscous contrast enhancing media with infusion agent, for example, embolization material including saline and embolization beads, for example, in a volumetric ratio of 50:50, thereby producing a viscous fluidic infusion suspension of embolization beads and contrast enhancing media diluted to a chosen degree. In exemplary embodiments, the contrast enhancing material (agent) (such as contrast enhancing material (agent) CM shown in FIG. 1A) may be, or include, any of various different types or kinds of contrast media, for example, Visipaque™ (iodixanol), or Omnipaque™ (iohexol), among many other suitable types and kinds of contrast media.

One or more opening 116 includes a pore having a cross sectional dimension less than minimal diameter of the infusion agent embolization material (e.g., bead diameter). Such cross sectional dimension is, for example, less than about 500 microns (μm), or, equal to or less than about 100 microns (μm), or, equal to or less than about 40 microns (μm). In exemplary embodiments, the cross section dimension is in a range of between about 20 microns (μm) and about 30 microns (μm), for example, about 28 microns (μm). For example, as shown, each pore is located at end of a channel being angled relative to a long axis of lumen 114 or/and relative to a radial axis thereof at a cross section adjacent thereto. In exemplary embodiments, at least two pores are angularly located in different directions such that a first stream of the infusion suspension in immediate vicinity of a first pore at least partially intersects a second stream of the infusion suspension in immediate vicinity of a second pore.

In some embodiments, lumen 114 is configured to deliver a suspension of infusion fluid 117 and infusion agent 113 (e.g., in a form of beads). In some embodiments, a distal outlet of microcatheter 110 is shaped or/and sized to allow passage therethrough of the suspension of infusion fluid 117 and the beads 113, and at least one of side opening 116 is shaped or/and sized to allow passage therethrough of infusion fluid 117, and to block passage therethrough of most or all beads 113, for example if at least one cross sectional dimension (e.g., length, width, diameter) of the pore in this at least one opening is less than a minimal diameter of the beads.

In some embodiments, each side opening 116 is shaped or/and sized to allow passage therethrough of infusion fluid 117, and to block passage therethrough of beads 113, during flow of the infusion suspension through the distal outlet. In some other embodiments, each side opening 116 is shaped or/and sized to allow passage therethrough of infusion fluid 117, and to block passage therethrough of beads 113, during conditions when the infusion suspension is blocked or interrupted from flowing through the distal outlet.

In some embodiments, a total opened cross section of all side openings 116 is equal to or greater than a smallest cross section of lumen 114 and the distal outlet.

In some embodiments, infusion fluid 117 at normal body temperature has an average viscosity of at least about 0.8 mPa·s, or at least about 5 mPa·s, or at least about 10 mPa·s, or at least about 20 mPa·s. In exemplary embodiments, infusion fluid 117 is pre-heated, for example, to a temperature higher than about 37° C., before reaching tubular wall 115 distal portion in lumen 114.

In some embodiments, a farthest distal side opening 116 is located within a range of between about 0 mm and about 20 mm, or within a range of between about 0 mm and about 10 mm, or within a range of between about 0 mm and about 5 mm, proximally to the distal outlet.

Valve mechanism 112 is configured to cover side openings 116 when pressure inside tubular wall 115 distal portion is less than a predetermined pressure, and to uncover side openings 116 when pressure inside the tubular wall distal portion is greater than the predetermined pressure. Internal pressure may be built using an orifice or a narrowing (as shown in FIGS. 6A-6D, for example) at the distal outlet. In some embodiments, valve mechanism 112 includes a cover 118 configured to cover the plurality of side openings 116 and to prevent passage therethrough of fluids, and configured to uncover the plurality of side openings 116 when tubular wall 115 section is immersed in a proximally flowing fluid, such as for example, when it is provided in the small blood vessel when retrograded flow occurs. The tubular wall section 115 may include a space between the plurality of side openings 116 and cover 118, which is sized to accumulate a predetermined maximal volume of infusion fluid 117 absent of beads 113. Such predetermined maximal volume may be in a range of between about 0 ml and about 1 ml. In exemplary embodiments, the predetermined maximal volume is at least about 1 ml, or at least about 5 ml, or at least about 10 ml.

Cover 118 may be fabricated from metal, for example, a super-elastic metal alloy (e.g., nitinol or stainless steel), or from a polymer (e.g., PTFE, ePTFE, polyester, FEP, urethane, Pebax, or Pellethane) for example, rigid or semi-rigid. In some embodiments, cover 118 may increase the overall microcatheter diameter by an amount between about 0.5 mm and about 1 mm, for example, about 0.8 mm, when cover 118 is in a closed position. In some embodiments, cover 118 may increase the overall microcatheter diameter by an amount between about 1 mm and about 10 mm, for example, by about 5 mm, when cover 118 is in an opened position. In exemplary embodiments, cover 118 has a length in a range of between about 1 mm and about 5 m. In exemplary embodiments, cover 118 has a thickness in a range of between about 20 microns and about 500 microns. In exemplary embodiments, cover 118 is attached to tubular wall 115 via at least one of: laser cut hinges, gluing, melting, and heat shrinking of an outer layer.

FIGS. 9A-9B schematically illustrate side cut views of exemplary embodiments of a distal end of an exemplary microcatheter 120, particularly showing an exemplary embodiment of a valve mechanism 121 configured to cover (FIG. 9A) and uncover (FIG. 9B) side openings 122 provided at an infusion agent flow disruption section 123. Microcatheter 120 may be an embolization microcatheter sized and configured for delivering infusion agent 124 (e.g., in the form of beads) in a small blood vessel towards a target bodily part. Microcatheter 120 includes a lumen 125 surrounded by a tubular wall 126 having an outer diameter and opened at both ends. In some embodiments, tubular wall 126 is sized for unhindered insertion into a small blood vessel, such as a celiac or hepatic artery. In some embodiments, outer diameter of microcatheter 120 is equal to or less than about 2 mm, or, equal to or less than about 1 mm. In some embodiments, microcatheter 120 has an external diameter equal to the diameter of a commercially available microcatheter, such as a 2.1 French catheter, a 2.7 French catheter, or a 2.9 French catheter.

Infusion agent 124 may include at least one of liquid embolic agents (e.g., Onyx™ by Covidien, n-butyle-2-cyanoacrylate, or ethiodized oil), sclerosing agents (e.g., ethanol, ethanolamine oleate, or sodium tetradecyl sulfate), or particulate embolic agents (e.g., hemostatic absorbable gelatin, polyvinyl alcohol, or acrylic gelatin microspheres). In exemplary embodiments, infusion agent 124 is of particulate form (e.g., non-spherical particles, or microspheres) having an average size (long dimension or diameter) in a range of between about 30 microns (μ) and about 1500 microns (μ). In exemplary embodiments, infusion agent 124 has a compressibility in a range of between about 10% and about 40%. For example, polyvinyl alcohol (PVA) type infusion agent has a compressibility in a range of between about 20% and about 30%.

Infusion agent flow disruption section 123 is configured to disrupt passage therethrough of an incoming retrograded flow 127 of infusion agent, during continuous delivery of infusion agent 124 through distal outlet of microcatheter 120. Flow disruption section 123 is configured to block, or/and cause turbulence in, incoming retrograded flow 127 of the infusion agent, thereby increasing local pressure thereabout.

(Side) openings 122 are distributed around or/and along flow disruption section 123, each opening is shaped or/and sized to allow passage therethrough of an infusion fluid 128, and to block passage therethrough of the infusion agent 124.

Infusion fluid 128, in exemplary embodiments, includes a contrast enhancing agent, for example, diluted to a certain degree such as by saline. In some instances, the medical practitioner may mix together a viscous contrast enhancing media with infusion agent including saline and embolization beads, for example, in a volumetric ratio of 50:50, thereby producing a viscous fluidic infusion suspension of embolization beads and contrast enhancing media diluted to a chosen degree. In exemplary embodiments, the contrast enhancing material (agent) (such as contrast enhancing material (agent) CM shown in FIG. 1A) may be, or include, any of various different types or kinds of contrast media, for example, Visipaque™ (iodixanol), or Omnipaque™ (iohexol), among many other suitable types and kinds of contrast media.

One or more opening 122 includes a pore or/and slits having a cross sectional dimension less than minimal diameter of the infusion agent (e.g., beads diameter). Such cross sectional dimension is, for example, less than about 500 microns (μm), or, equal to or less than about 100 microns (μm), or, equal to or less than about 40 microns (μm). In exemplary embodiments, the cross sectional dimension is in a range of between about 20 microns (μm) and about 30 microns (μm), for example, about 28 microns (μm). For example, as shown, each pore is located at end of a channel being angled relative to a long axis of lumen 125 or/and relative to a radial axis thereof at a cross section adjacent thereto. In exemplary embodiments, at least two pores are angularly located in different directions such that a first stream of the infusion fluid in immediate vicinity of a first pore at least partially intersects a second stream of the infusion fluid in immediate vicinity of a second pore.

In some embodiments, lumen 125 is configured to deliver a suspension of infusion fluid 128 and infusion agent 124 (e.g., in a form of beads). In some embodiments, a distal outlet 129 of microcatheter 120 is shaped or/and sized to allow passage therethrough of the infusion suspension of infusion fluid 128 and the beads 124, and each side opening 122 is shaped or/and sized to allow passage therethrough of infusion fluid 128, and to block passage therethrough of beads 124, for example if a cross sectional dimension of the pore in each opening is less than a minimal diameter of the beads.

In some embodiments, each side opening 122 is shaped or/and sized to allow passage therethrough of infusion fluid 128, and to block passage therethrough of beads 124, during flow of the suspension through distal outlet 129. In some other embodiments, each side opening 122 is shaped or/and sized to allow passage therethrough of infusion fluid 128, and to block passage therethrough of beads 124, during conditions when the infusion suspension is blocked or interrupted from flowing through distal outlet 129.

In some embodiments, a total opened cross section of all side openings 122 is equal to or greater than a smallest cross section of lumen 125 and distal outlet 129.

In some embodiments, infusion fluid 128 at normal body temperature has an average viscosity of at least about 0.8 mPa·s, or at least about 5 mPa·s, or at least about 10 mPa·s, or at least about 20 mPa·s. In exemplary embodiments, infusion fluid 128 is pre-heated, for example, to a temperature higher than about 37° C., before reaching tubular wall 126 distal portion in lumen 125.

In some embodiments, a farthest distal side opening 122 is located within a range of between about 0 mm and about 20 mm, or within a range of between about 0 mm and about 10 mm, or within a range of between about 0 mm and about 5 mm, proximally to the distal outlet.

Valve mechanism 121 is configured to cover side openings 122 when pressure inside tubular wall 126 distal portion is less than a predetermined pressure, and to uncover side openings 122 when pressure inside tubular wall distal portion is greater than the predetermined pressure. Internal pressure may be built using an orifice or a narrowing (as shown in FIGS. 6A-6D, for example) at distal outlet 129. Valve mechanism 121 may include a normally-withdrawn pop-out cover 130, for example, connected to a tension spring, configured to fully withdraw into tubular wall 126 (FIG. 9A) at an internal pressure less than the predetermined pressure and to at least partially protrude at an internal pressure exceeding the predetermined pressure. Valve mechanism 121 may also be configured for extending cover 130 in order to distance distal outlet 129 away from side openings 122.

Figure 10A:
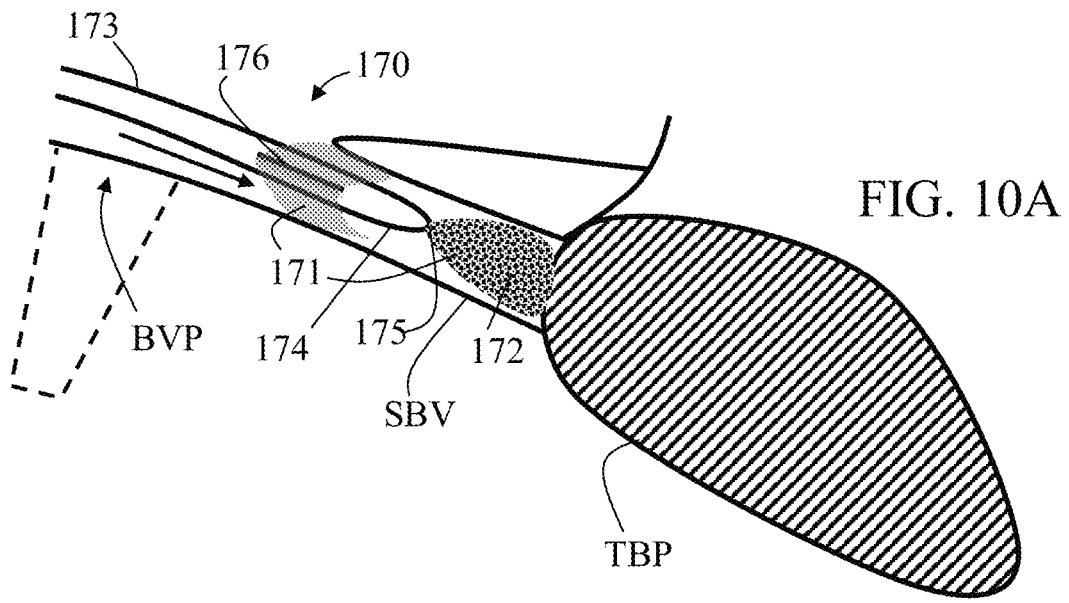
FIGS. 10A-10B are schematic side cut views representing possible scenarios of implementing exemplary embodiments of a method for performing local embolization in a small blood vessel feeding a target bodily part, particularly highlighting detecting an indication of presence of infusion fluid in a blood vessel portion upstream to the small blood vessel, in accordance with some embodiments of the invention.
Figure 10B:
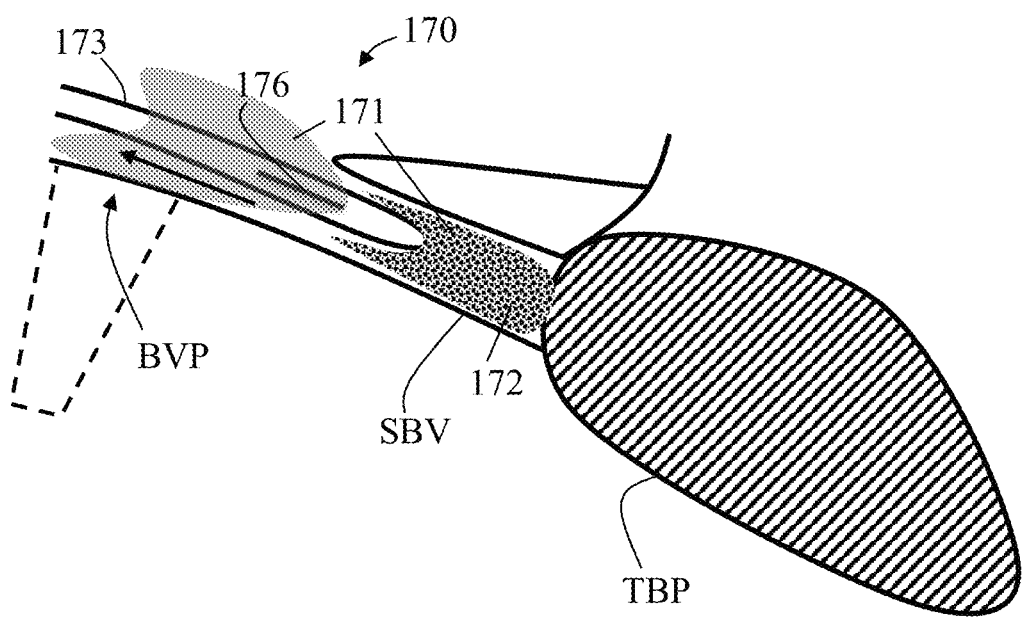

FIGS. 10A-10B schematically illustrate side cut views representing possible scenarios of implementing exemplary embodiments of a method for performing local embolization in a small blood vessel SBV feeding a (for example, cancerous) target bodily part TBP. Such exemplary embodiments include detecting an indication of presence of infusion fluid in a blood vessel portion BVP upstream to small blood vessel SBV. A microcatheter 170 which may be used in this method, configured for positioning and delivering infusion agent (e.g., embolization material and/or contrast enhancing material) in small blood vessel SBV, includes a lumen configured to deliver an infusion suspension of an infusion fluid 171 and infusion agent 172 (e.g., in a form of beads), the lumen is surrounded by a tubular wall 173 having an outer diameter and opened at both ends. In some embodiments, infusion fluid 171 includes a contrast enhancing agent, so it can be detected under x-ray imaging. A distal portion of tubular wall 173 ends with a tip 174 enclosing a distal outlet 175. At least one side opening 176, having a total opened cross section, is, for example, positioned or/and distributed around or/and along a section of tubular wall 173 proximally to distal outlet 175. Distal outlet 175 is shaped or/and sized to allow passage therethrough of the infusion suspension of infusion fluid 171 and beads 172, and each side opening 176 is shaped or/and sized to allow passage therethrough of infusion fluid 171, and to block passage therethrough of beads 172.

Microcatheter 170 is passed into small blood vessel SBV until tip 174 is in a chosen distance to target bodily part TBP. The infusion suspension of infusion fluid 171 and beads 172 may then be delivered via distal outlet 175 towards target bodily part TBP. Before, after or in parallel to infusion suspension delivery, a volume of infusion fluid 171 is infused through side openings 176 while beads 172 are blocked from passing therethrough, as shown in FIG. 10A.

In some embodiments, the infusing occurs following blood flow reflux from the small blood vessel SBV towards blood vessel portion BVP (FIG. 10B). Blood vessel portion BVP is selected, being upstream to small blood vessel SBV, and is then monitored using an imaging technique. In some embodiments, x-ray (e.g., fluoroscopy), ultrasound or/and Doppler techniques are used for the monitoring, thus blood vessel portion BVP is chosen also based on ease or/and feasibility of applying any of these techniques, accordingly. Via monitoring, the medical practitioner may seek to detect an indication of presence of infusion fluid 171 in blood vessel portion BVP so, in response, he may stop any further delivery of infusion suspension.

In exemplary embodiments, blood vessel portion BVP distance from small blood vessel SBV is determined with a (e.g., predetermined) minimal effectively imaged quantity of infusion fluid 171 volume, originating from side openings 176, flowing into blood vessel portion BVP before the suspension, which originates from distal outlet 175, reaches blood vessel portion BVP following blood flow reflux from small blood vessel SBV towards blood vessel portion BVP. The required distance may be up to about 10 mm, or at least about 10 mm, or at least about 20 mm, or at least about 50 mm.

Each of the following terms written in singular grammatical form: 'a', 'an', and 'the', as used herein, means 'at least one', or 'one or more'. Use of the phrase 'one or more' herein does not alter this intended meaning of 'a', 'an', or 'the'. Accordingly, the terms 'a', 'an', and 'the', as used herein, may also refer to, and encompass, a plurality of the stated entity or object, unless otherwise specifically defined or stated herein, or, unless the context clearly dictates otherwise. For example, the phrases: 'a unit', 'a device', 'an assembly', 'a mechanism', 'a component', 'an element', and 'a step or procedure', as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: 'includes', 'including', 'has', 'having', 'comprises', and 'comprising', and, their linguistic/grammatical variants, derivatives, or/and conjugates, as used herein, means 'including, but not limited to', and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase 'consisting essentially of'.

Each of the phrases 'consisting of' and 'consists of', as used herein, means 'including and limited to'.

The phrase 'consisting essentially of', as used herein, means that the stated entity or item (system, system unit, system sub-unit, device, assembly, sub-assembly, mechanism, structure, component, element, or, peripheral equipment, utility, accessory, or material, method or process, step or procedure, sub-step or sub-procedure), which is an entirety or part of an exemplary embodiment of the disclosed invention, or/and which is used for implementing an exemplary embodiment of the disclosed invention, may include at least one additional 'feature or characteristic' being a system unit, system sub-unit, device, assembly, sub-assembly, mechanism, structure, component, or element, or, peripheral equipment, utility, accessory, or material, step or procedure, sub-step or sub-procedure), but only if each such additional 'feature or characteristic' does not materially alter the basic novel and inventive characteristics or special technical features, of the claimed entity or item.

The term 'method', as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Throughout this disclosure, a numerical value of a parameter, feature, characteristic, object, or dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably.

The term 'about', as used herein, refers to ±10% of the stated numerical value.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment, may also be illustratively described and presented in the context or format of a plurality of separate embodiments.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An embolization microcatheter, comprising an elongated body, a proximal inlet and a distal head section, the distal head section comprising:
   (a) a tip having a distal outlet configured for allowing outflow of particles suspended in a fluid delivered to the microcatheter through the proximal inlet; and
   (b) a filter section comprising a plurality of slits formed around and along a wall of said filter section, wherein a width of each of said plurality of slits is equal to or less than about 100 microns, thereby preventing outflow at least of particles having a bead diameter ranging between 100 to 1500 microns, while allowing selective lateral outflow of said fluid, wherein said lateral outflow of said fluid is configured to disrupt retrograded flow of said particles, delivered through the distal outlet around a periphery of said tip.

2. The microcatheter of claim 1, wherein the filter section comprises a material being more flexible than that of other wall portions of said embolization microcatheter's wall.

3. The microcatheter of claim 2, wherein the filter section is configured to allow selective lateral outflow of said fluid while blocking passage of said particles, when said distal head section is straight, curved and bent.

4. The microcatheter according to of claim 1, wherein said microcatheter is configured as a single integrated structure.

5. The microcatheter of claim 1, wherein a distal most of said plurality of slits is located within a range of between about 0 mm and about 20 mm, proximally to the distal outlet.

6. The microcatheter of claim 1, wherein a distal most of said plurality of slits is located within a range of between about 0 mm and about 10 mm, proximally to the distal outlet.

7. The microcatheter of claim 1, wherein said plurality of slits are formed along a longitudinal axis of the filter section.

8. The microcatheter of claim 1, wherein said plurality of slits are angled relative to a long axis of said filter section or/and relative to a radial axis of said filter section.

9. An embolization microcatheter, comprising an elongated body, a proximal inlet and a distal head section, the distal head section comprising:
   (a) a tip having a distal outlet configured for allowing outflow of particles suspended in a fluid delivered to the microcatheter through the proximal inlet; and
   (b) a filter section comprising a plurality of slits formed around and along a wall of said filter section, the slits configured to prevent outflow of the particles, while allowing lateral outflow of the fluid, wherein the lateral outflow of the fluid is configured to disrupt retrograded flow of the particles, delivered through the distal outlet around a periphery of the tip,
   wherein a total opened cross section of the plurality of slits is equal to or greater than a cross section of the distal outlet, thereby allowing sufficient outflow of the fluid, through the plurality of slits to disrupt retrograded flow of particles, delivered through the distal outlet, around a periphery of the tip.

10. The microcatheter of claim 9, wherein the elongated body has an outer diameter equal to or less than about 1 mm.

11. The microcatheter of claim 9, wherein the filter section comprises a material being more flexible than that of other wall portions of said embolization microcatheter's wall.

12. The microcatheter of claim 9, wherein the elongated body has an outer diameter equal to or less than about 1 mm.

13. An embolization microcatheter, comprising: an elongated body, a proximal inlet and a distal head section, the distal head section comprising:
   (a) a tip having a distal outlet configured for allowing outflow of particles suspended in a fluid delivered to the microcatheter through the proximal inlet; and
   (b) a filter section comprising a plurality of slits formed around and along a wall of the filter section, the slits configured to allow selective lateral outflow of the fluid while blocking passage of the particles, wherein the lateral outflow of the fluid is configured to disrupt retrograded flow of the particles, delivered through the distal outlet around a periphery of the tip;
   wherein the filter section is pressure sensitive and configured to disrupt retrograded flow of the infusion agent only when pressure inside the distal head section equals a predetermined expansion pressure; and
   wherein the embolization microcatheter further comprises a valve mechanism configured to cover side openings provided at said filter section when pressure inside said distal head section is less than said predetermined pressure, and to uncover said side openings when pressure inside said distal head section is greater than said predetermined pressure.

14. The microcatheter of claim 13, wherein said filter section is configured to stretch from a first average diameter to a second average diameter greater than an outer diameter of the microcatheter when pressure inside said distal head section equals said predetermined pressure, and to collapse back to said first average diameter when said pressure inside said distal head section is less than said predetermined pressure, during said continuous delivery of said infusion suspension from said reservoir to said tip before, during, and after said stretching and collapsing.

15. The microcatheter of claim 13, wherein, under a selected inner pressure being greater than said expansion pressure and less than ambient pressure, said filter section stretches in response to a systole and collapses in response to a diastole.

16. A method for performing local embolization in a small blood vessel, the method comprising:
   positioning an embolization microcatheter within a target blood vessel, the embolization microcatheter comprising an elongated body comprising a proximal inlet and a distal head section comprising:
      (a) a tip having a distal outlet configured for allowing outflow of particles suspended in a fluid delivered to the microcatheter through the proximal inlet; and
      (b) a filter section comprising a plurality of slits formed around and along a wall of said filter section;
      wherein each of said plurality of slits has a minimal cross section of 100 microns or less thereby preventing outflow at least of particles having a bead diameter ranging between 100 to 1500 microns,
   delivering embolization particles suspended in a fluid through a lumen of the microcatheter.

17. The method of claim 16, further comprising a preliminary step of locating of the target blood vessel using an imaging technique.

18. The method of claim 16, wherein the particles comprise embolization beads, radioactive embolization beads, radio-opaque embolization beads, chemotherapeutic embolization beads drug eluting embolization beads or any combination thereof.

19. The method of claim 16, wherein the fluid comprises saline, a contrast enhancing agent, lipiodol or any combination thereof.

20. The method of claim 16, wherein the selective outflow of the fluid is effected while maintaining said distal head section in a straight, curved or bent configuration.

* * * * *